(12) United States Patent
Cole et al.

(10) Patent No.: US 11,612,421 B1
(45) Date of Patent: Mar. 28, 2023

(54) TENSIONER-BALANCER FOR KNEE JOINT

(71) Applicant: Little Engine, LLC, Belmont, NC (US)

(72) Inventors: J. Dean Cole, Orlando, FL (US); Franz W. Kellar, Gastonia, NC (US); Harold L. Crowder, Concord, NC (US); Michael D. Bissette, Belmont, NC (US); Franz Austen Kellar, Gastonia, NC (US)

(73) Assignee: Little Engine, LLC, Belmont, NC (US)

( * ) Notice: Subject to any disclaimer, the term of this patent is extended or adjusted under 35 U.S.C. 154(b) by 0 days.

(21) Appl. No.: 17/554,616

(22) Filed: Dec. 17, 2021

Related U.S. Application Data

(60) Provisional application No. 63/246,168, filed on Sep. 20, 2021.

(51) Int. Cl.
    *A61B 17/80*     (2006.01)
    *A61B 17/70*     (2006.01)
    (Continued)

(52) U.S. Cl.
    CPC ...... *A61B 17/8004* (2013.01); *A61B 17/7023* (2013.01); *A61B 2017/00415* (2013.01); *A61B 2017/681* (2013.01)

(58) Field of Classification Search
    CPC . A61B 17/025; A61B 17/723; A61B 17/8004; A61B 2017/0256;
(Continued)

(56) References Cited

U.S. PATENT DOCUMENTS

| | | |
|---|---|---|
| 5,713,897 A | 2/1998 | Goble et al. |
| 5,935,129 A | 8/1999 | McDevitt et al. |
| (Continued) | | |

FOREIGN PATENT DOCUMENTS

| | | |
|---|---|---|
| WO | 2014188184 | 11/2014 |
| WO | 2017195046 | 11/2017 |

OTHER PUBLICATIONS

Attune Knee System, CAS Surgical Technique, Published 2014, accessed at "http://synthes.vo.llnwd.net/o16/LLNWMB8/US%20Mobile/Synthes%20North%20America/Product%20Support%20Materials/Technique%20Guides/DSUS-JRC-0514-0141%20ATTUNE_CAS_ST.pdf".

(Continued)

*Primary Examiner* — Christopher D. Prone
(74) *Attorney, Agent, or Firm* — Trego, Hines & Ladenheim, PLLC

(57) ABSTRACT

A knee gap tensioning apparatus includes: a tensioner-balancer, including: a baseplate; a top plate; and a linkage operable to move the top plate relative to the bottom plate between retracted and extended positions in response to application of an actuating force, the linkage including: a first toggle linkage, including: a lower link having a first end pivotally connected to the baseplate; an upper link having a first end pivotally connected to the top plate, wherein second ends of the first and second links are pivotally connected to each other; a second toggle linkage, including: a lower link having a first end pivotally connected to the baseplate; an upper link having a first end pivotally connected to the top plate, wherein second ends of the first and second links are pivotally connected to each other; and a connector linkage interconnecting the first and second toggle linkages.

14 Claims, 37 Drawing Sheets

(51) Int. Cl.
*A61B 17/00* (2006.01)
*A61B 17/68* (2006.01)

(58) Field of Classification Search
CPC .. A61B 2017/0268; A61B 2017/00415; A61B 2017/681; A61B 17/7023
See application file for complete search history.

(56) References Cited

U.S. PATENT DOCUMENTS

| | | | |
|---|---|---|---|
| 6,022,377 | A | 2/2000 | Nuelle et al. |
| 6,162,234 | A | 12/2000 | Freedland et al. |
| 7,070,598 | B2* | 7/2006 | Lim .................. A61F 2/442 623/17.16 |
| 10,405,849 | B1 | 9/2019 | Cole et al. |
| 10,478,171 | B1 | 11/2019 | Cole et al. |
| 10,555,729 | B1 | 2/2020 | Cole et al. |
| 2001/0008971 | A1 | 7/2001 | Schwartz et al. |
| 2003/0032983 | A1 | 2/2003 | Bonutti et al. |
| 2005/0222488 | A1 | 10/2005 | Chang et al. |
| 2008/0051798 | A1 | 2/2008 | Colquhoun et al. |
| 2008/0114367 | A1* | 5/2008 | Meyer .................. A61F 2/442 606/191 |
| 2008/0288060 | A1 | 11/2008 | Kaye et al. |
| 2010/0250571 | A1* | 9/2010 | Pierce ................ A61B 5/4528 600/587 |
| 2011/0093081 | A1 | 4/2011 | Chana et al. |
| 2013/0102929 | A1 | 4/2013 | Haight et al. |
| 2014/0025081 | A1 | 1/2014 | Lorio et al. |
| 2014/0094715 | A1 | 4/2014 | Stein et al. |
| 2014/0194907 | A1 | 7/2014 | Bonutti et al. |
| 2015/0105782 | A1 | 4/2015 | D'Lima et al. |
| 2016/0007909 | A1 | 1/2016 | Singh et al. |
| 2016/0030156 | A1 | 2/2016 | Cole |
| 2016/0106409 | A1 | 4/2016 | Moholkar |
| 2016/0278944 | A1 | 9/2016 | D'Lima et al. |
| 2017/0065438 | A1 | 3/2017 | Burnikel |
| 2017/0172624 | A1* | 6/2017 | Brunner ............ A61B 17/7016 |
| 2017/0312099 | A1 | 11/2017 | Paziesnyek |
| 2018/0049622 | A1 | 2/2018 | Ryan et al. |
| 2018/0177612 | A1 | 6/2018 | Masei et al. |
| 2018/0296232 | A1 | 10/2018 | Nielsen et al. |
| 2019/0076273 | A1 | 3/2019 | Goodchild et al. |
| 2019/0167447 | A1 | 6/2019 | Angibaud |
| 2019/0358056 | A1 | 11/2019 | Lerat et al. |

OTHER PUBLICATIONS

Bathis et al., "Flexion Gap Configuration in Total Knee Arthroplasty Following Hight Tibial Osteotomy", published online Sep. 30, 2004, International Orthopaedics (SICOT) 28: 366-369.

M. J. Winemaker, MD, FRCS (C), "Perfect Balance in Total Knee Arthroplasty, The Elusive Compromise", The Journal of Arthroplasty vol. 17. No. 1 2002, 2002, Churchill Livingstone, Canada.

International Search Report and Written Opinion from the International Searching Authority for International Patent Application No. PCT/US2019/061668 dated Jan. 14, 2020.

* cited by examiner

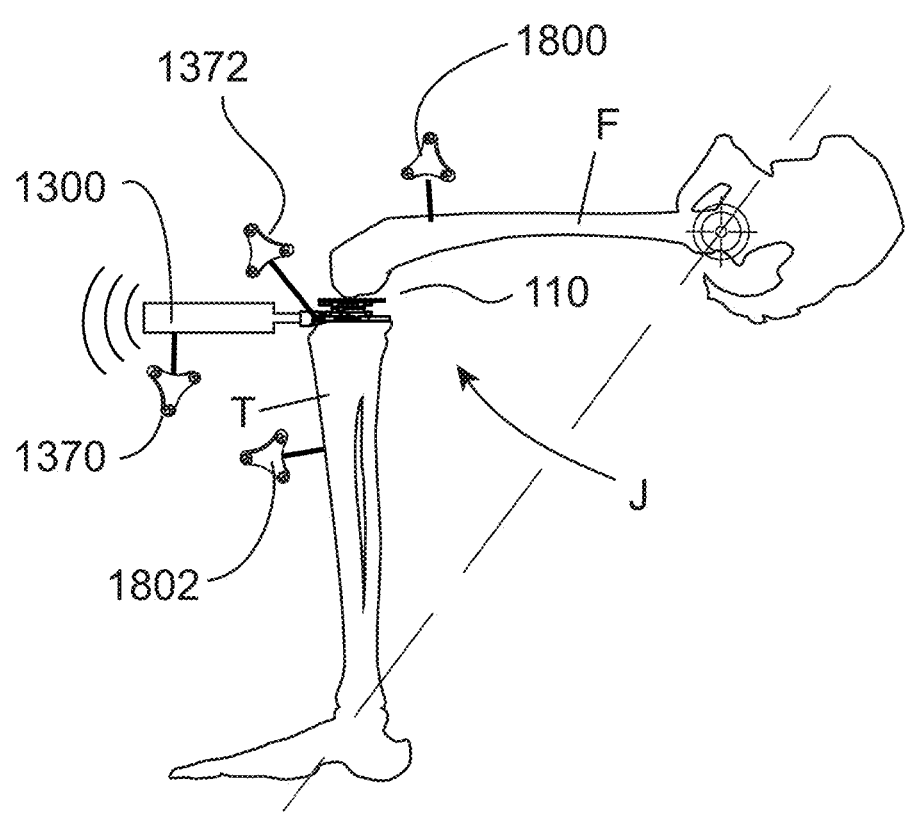
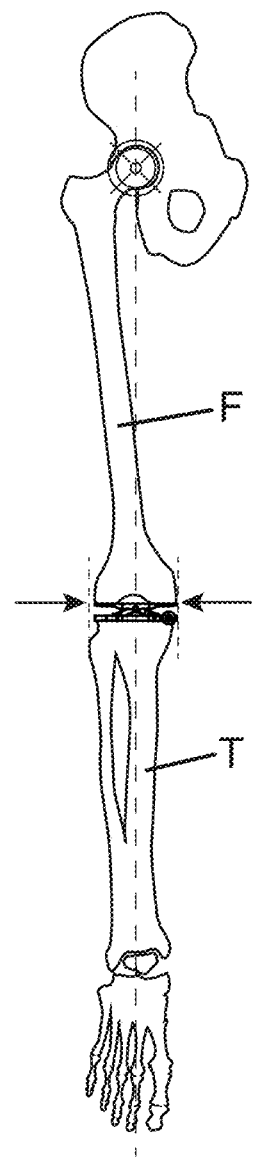
Fig. 62
Fig. 63

TENSIONER-BALANCER FOR KNEE JOINT

This application claims priority from Provisional Application 63/246,168, filed Sep. 20, 2021.

This invention relates generally to medical devices and instruments, and more particularly to a method for applying tension along or across a human knee joint to take measurements to repair, augment, or replace it.

BACKGROUND

Total knee arthroplasty ("TKA") is a procedure for treating an injured, diseased, or worn human knee joint. In a TKA, an endoprosthetic joint is implanted, replacing the bearing surfaces of the joint with artificial members. Proper alignment of the joint and substantially equal tension in the soft tissues surrounding the joint are important factors in producing a good surgical outcome.

A human knee joint "J" is shown in FIGS. 1-4. The joint J is prepared for implantation by cutting away portions of the femur "F" and the tibia "T". FIGS. 1 and 2 show the joint in extension, with cutting planes for a tibial cut 1 and a distal femoral cut 2. The tibial cut 1 and the distal formal cut 2 cooperate to define an extension gap "EG". FIGS. 3 and 4 show the joint J in flexion, with cutting plane 3 for a posterior cut. The tibial cut 1 and the posterior cut 3 cooperate to define a flexion gap "FG".

A goal of total knee arthroplasty is to obtain symmetric and balanced flexion and extension gaps FG, EG (in other words, two congruent rectangles). These gaps are generally measured in millimeters of separation, are further characterized by a varus or valgus angle measured in degrees, and are measured after the tibia cut, distal femoral cut, and posterior femoral cut have been done (to create flat surfaces from which to measure). It follows that, to achieve this balance, the ligament tension in the lateral and medial ligaments would be substantially equal on each side, and in each position; it also follows that the varus/valgus angle in flexion and extension would be 0°.

Some surgeons favor the use of a measured resection technique in which bone landmarks, such as the transepicondylar, the anterior-posterior, or the posterior condylar axes are used to determine proper femoral component rotation and subsequent gap balance. Others favor a "gap balancing technique" in which the femoral component is positioned parallel to the resected proximal tibia with each collateral ligament substantially equally tensioned to obtain a rectangular flexion gap.

One problem with prior art balancing techniques is that it is difficult and complex to achieve the proper balance. Current state-of-the-art gap balancing devices do not enable balancing with the patella in-place and are large, overly-complicated devices that work only with their respective knee systems.

BRIEF SUMMARY OF THE INVENTION

This problem is addressed by a using tensioner-balancer operable to apply a load to a gap between the bones of a joint and measure characteristics of the joint such as the resulting gap distance, angle between the bones, and/or loads.

According to one aspect of the technology described herein, a knee gap tensioning apparatus includes: a tensioner-balancer, including: a baseplate; a top plate; and a linkage interconnecting the baseplate and the top plate and operable to move the top plate relative to the bottom plate between retracted and extended positions in response to application of an actuating force, the linkage including: a first toggle linkage, including: a lower link having a first end and a second end, the first end pivotally connected to the baseplate; an upper link having a first end and a second end, the first end pivotally connected to the top plate, wherein the second ends of the first and second links are pivotally connected to each other; a second toggle linkage, including: a lower link having a first end and a second end, the first end pivotally connected to the baseplate; an upper link having a first end and a second end, the first end pivotally connected to the top plate, wherein the second ends of the first and second links are pivotally connected to each other; and a connector linkage interconnecting the first and second toggle linkages.

According to another aspect of the technology described herein, a method is described for imparting tension across a human knee joint which includes a femur bone, a tibia bone, and ligaments, wherein the ligaments are under anatomical tension to connect the femur and tibia together, creating a load-bearing articulating joint. The method includes: providing a tensioning device, including: a baseplate; a top plate; and a linkage positioned between and interconnecting the baseplate and the top plate and operable to move the top plate relative to the bottom plate between retracted and extended positions in response to application of an actuating force, wherein the top plate is pivotally connected to the linkage so as to be able to freely pivot about a single mechanical pivot axis to change its angular orientation relative to the base plate; positioning the tensioning device between the femur and the tibia; and applying an actuating force to the linkage to move the tensioning device towards the extended position, so as to impart a separating force driving the femur and tibia apart to extend the ligaments, wherein the actuating force causes individual links within the linkage to pivot about pivot axes that are fixed relative to the baseplate.

BRIEF DESCRIPTION OF THE DRAWINGS

The invention may be best understood by reference to the following description taken in conjunction with the accompanying drawing figures in which:

FIG. 62 is a view of a medial aspect of the human leg in flexion, with a tensioner-balancer inserted in the knee joint and tracking markers attached thereto;

FIG. 63 is a view of an anterior aspect of the human leg of FIG. 62 in extension.

DETAILED DESCRIPTION OF THE INVENTION

Figures 1, 2:
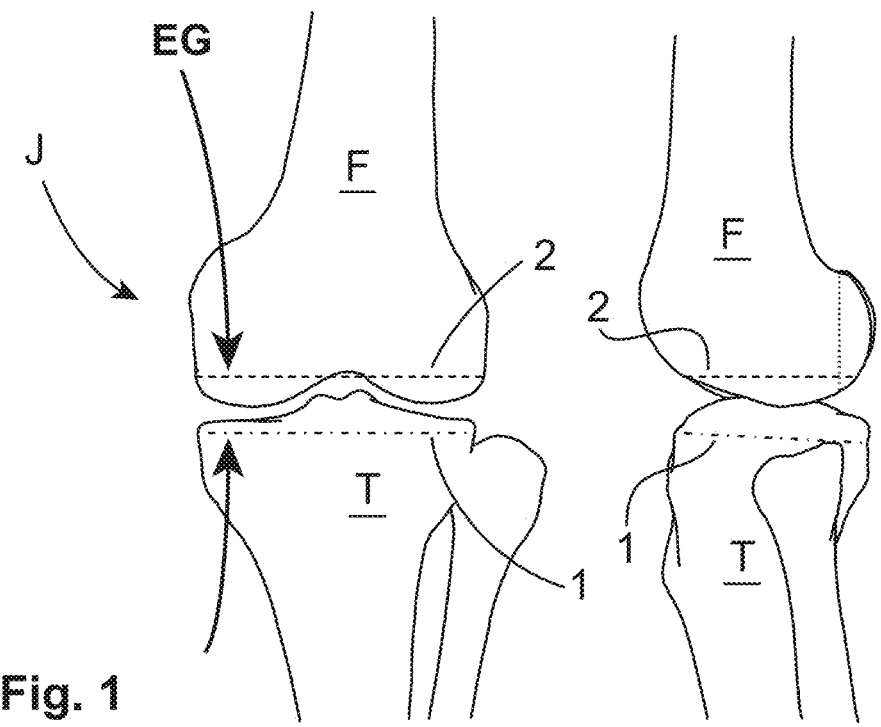
FIG. 1 is a view of the anterior aspect of the human knee joint in extension showing cutting planes for a total knee arthroplasty.
FIG. 2 is a view of the lateral aspect of the human knee joint of FIG. 1.
Figures 3, 4:
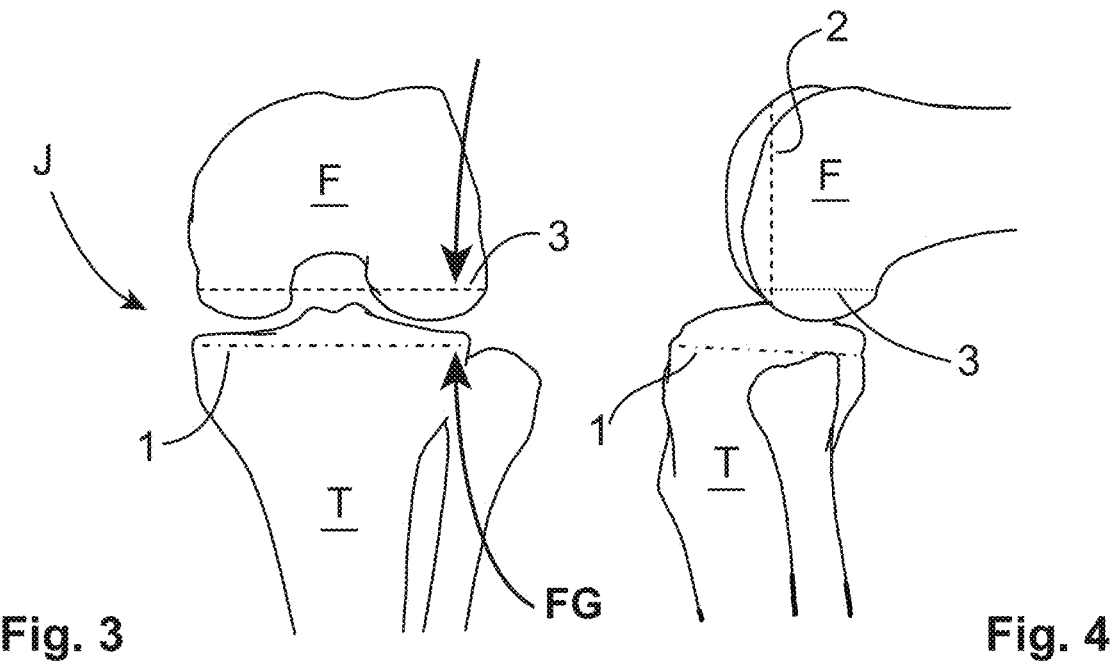
FIG. 3 is a view of the anterior aspect of the human knee joint in flexion showing cutting planes for a total knee arthroplasty.
FIG. 4 is a view of the lateral aspect of the human knee joint of FIG. 3.
Figure 5:
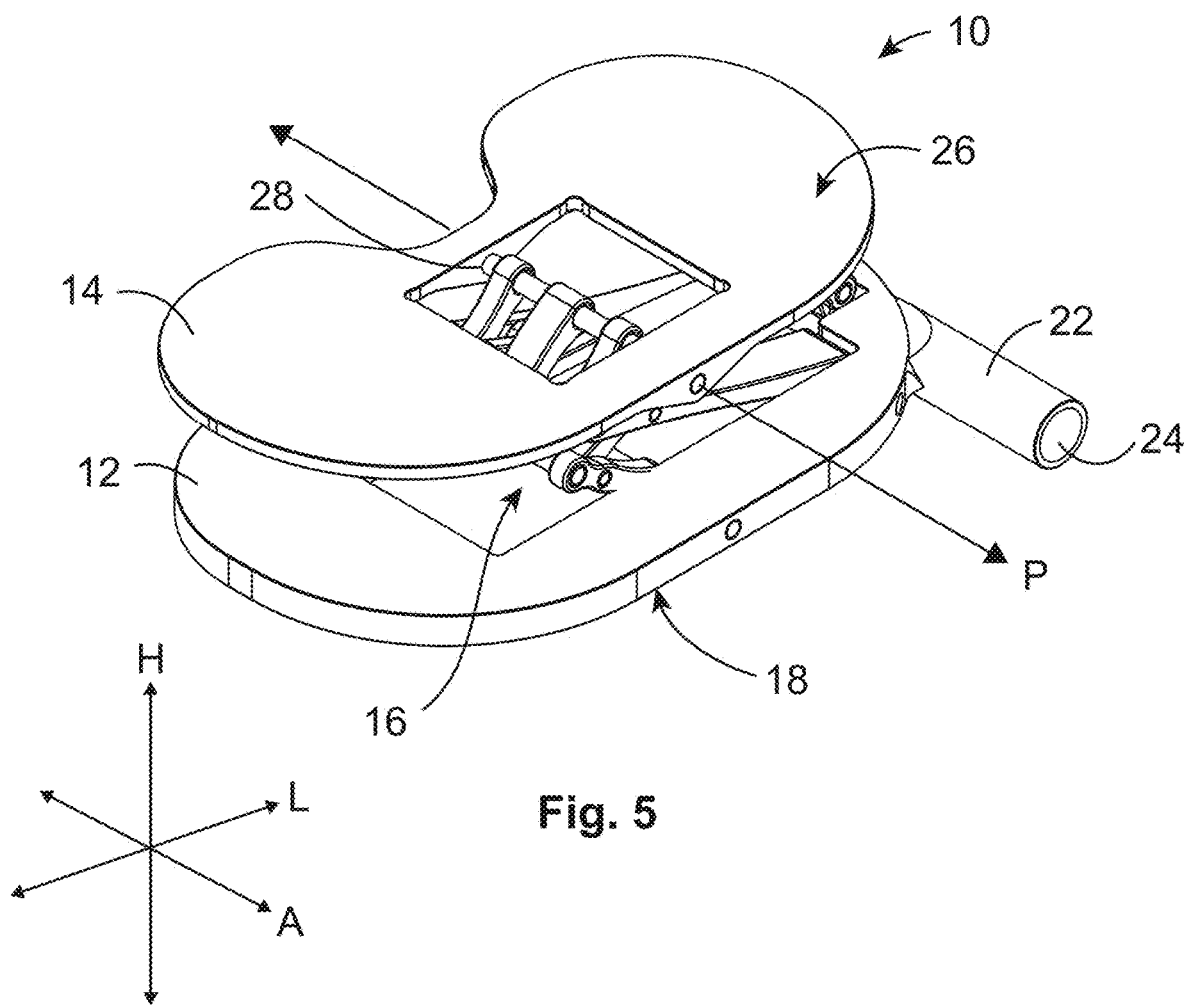
FIG. 5 is a perspective view of an exemplary tensioner-balancer, in an extended position.
Figure 6:
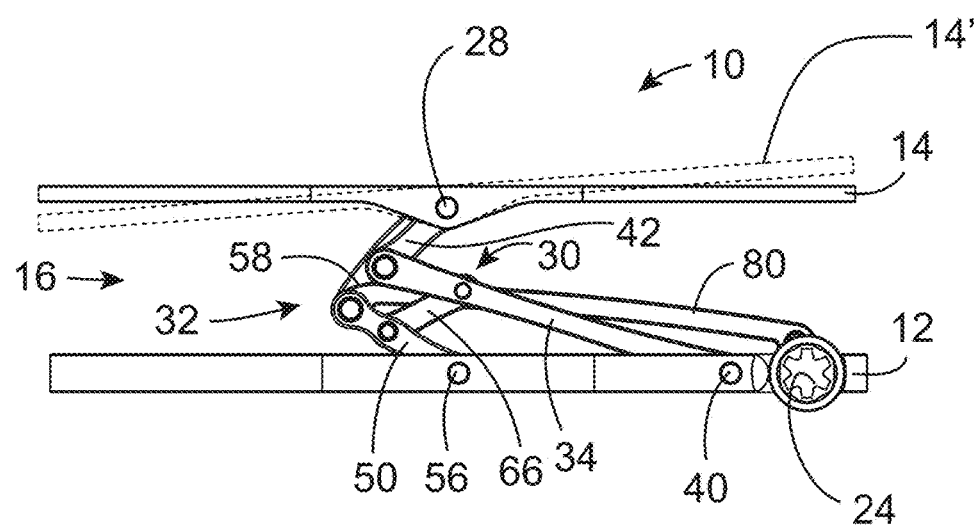
FIG. 6 is a front elevation view of the tensioner-balancer of FIG. 5.
Figure 7:
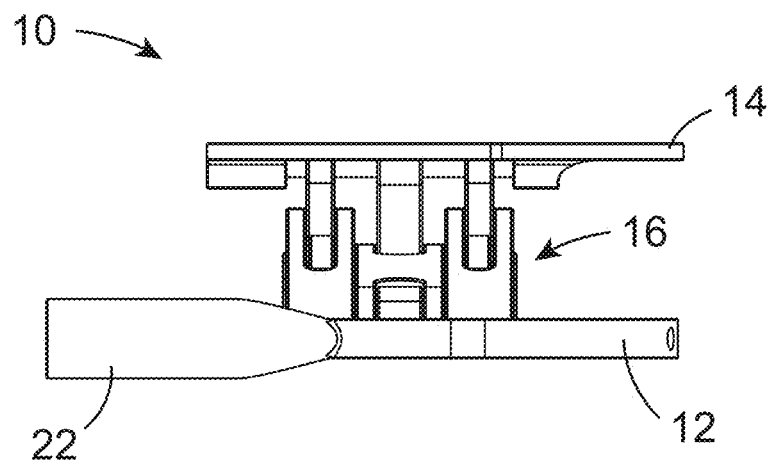
FIG. 7 is a side elevation view of the tensioner-balancer of FIG. 5.
Figure 8:
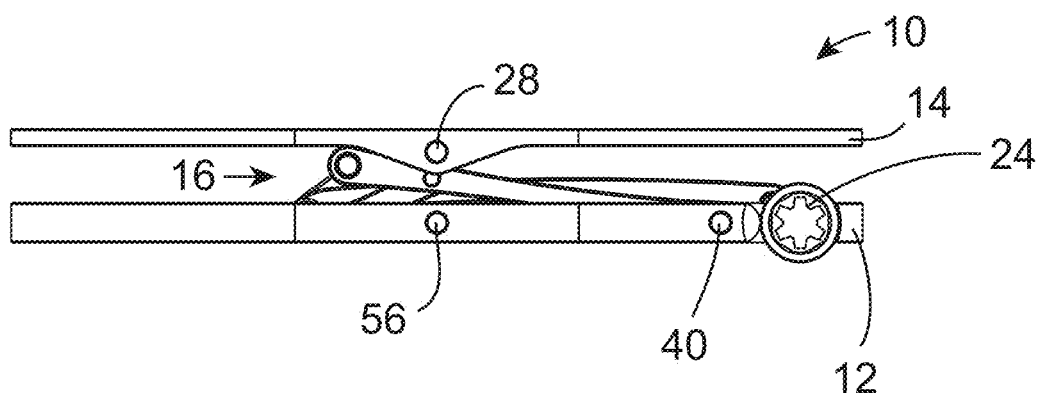
FIG. 8 is a front elevation view of the tensioner-balancer in FIG. 5, in a retracted position.
Figure 9:
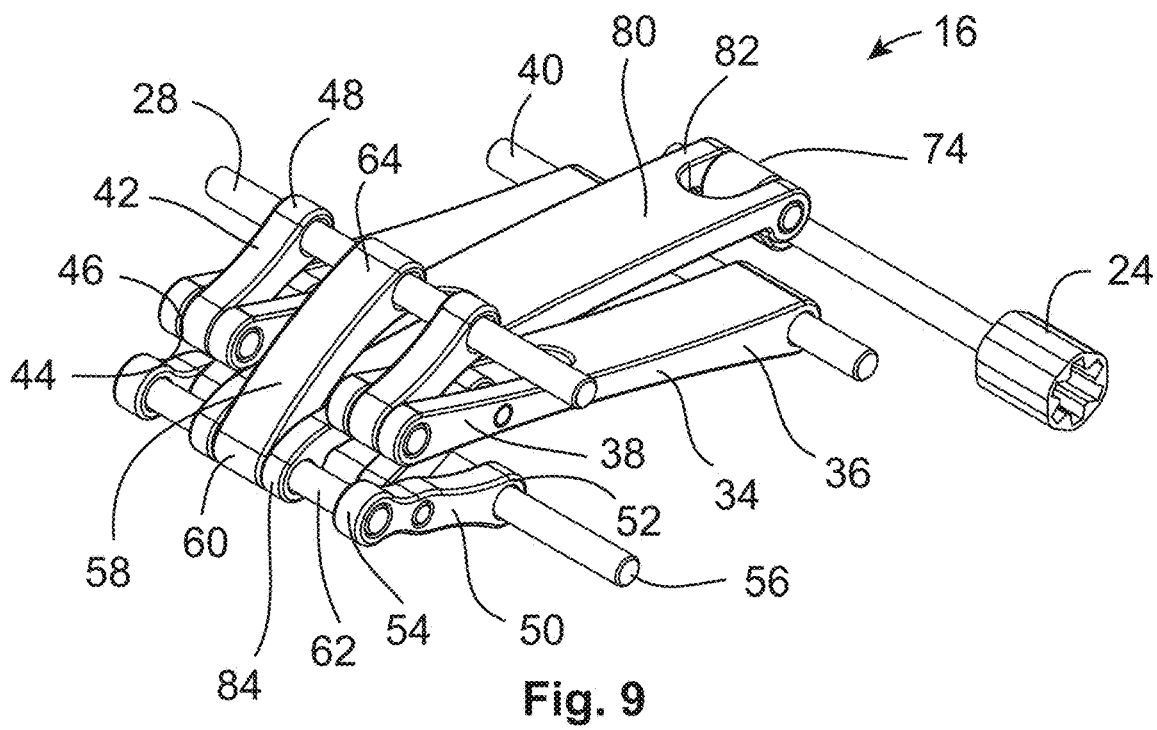
FIG. 9 is a perspective view of the internal linkage of the tensioner-balancer of FIG. 5.
Figure 10:
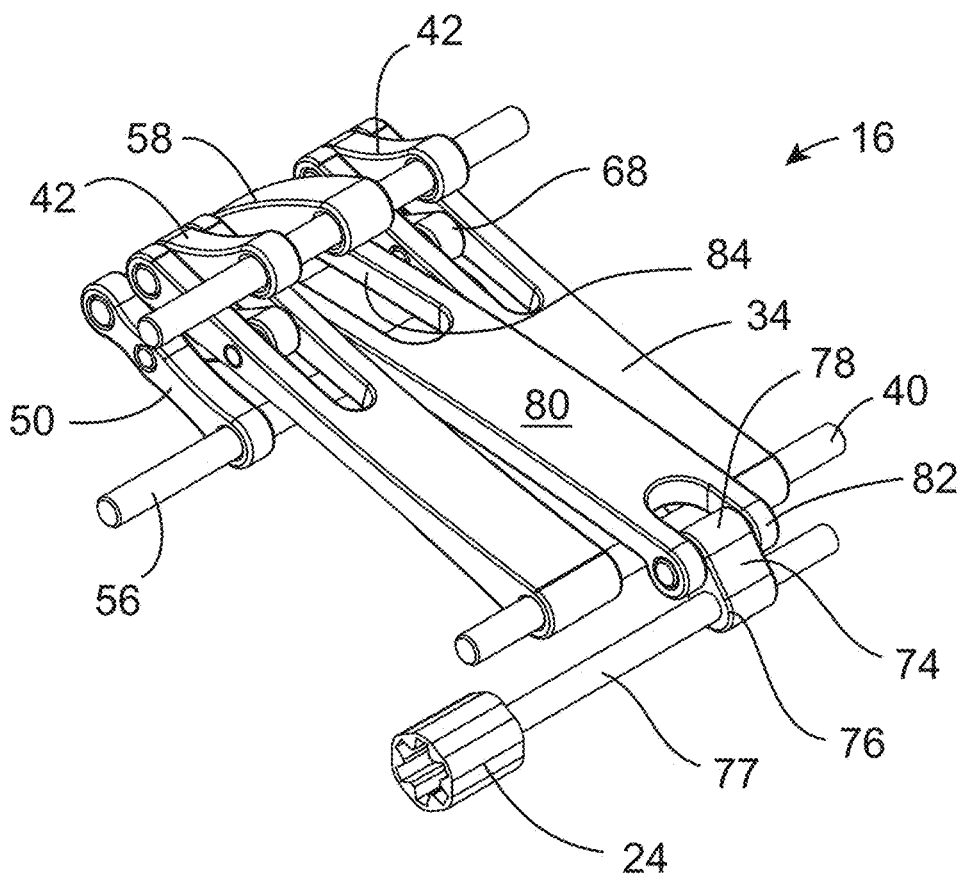
FIG. 10 is another perspective view of the internal linkage shown in FIG. 9.
Figure 11:
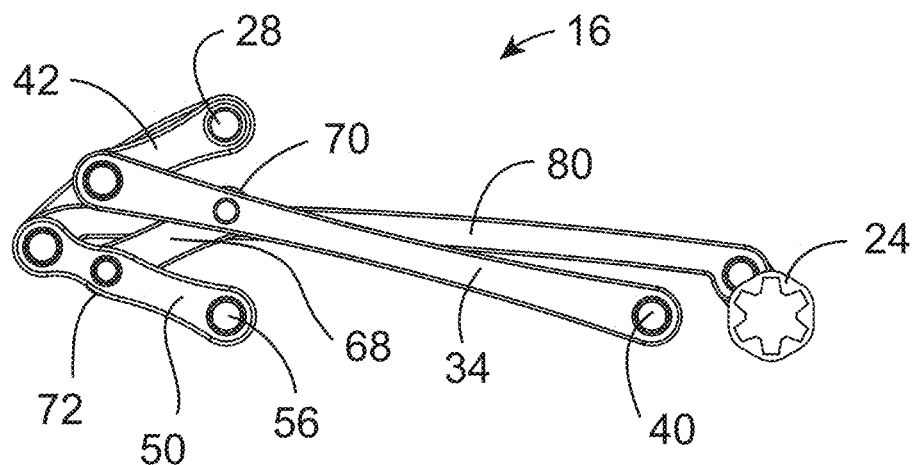
FIG. 11 is a front elevation view of the internal linkage shown in FIG. 9.
Figure 12:
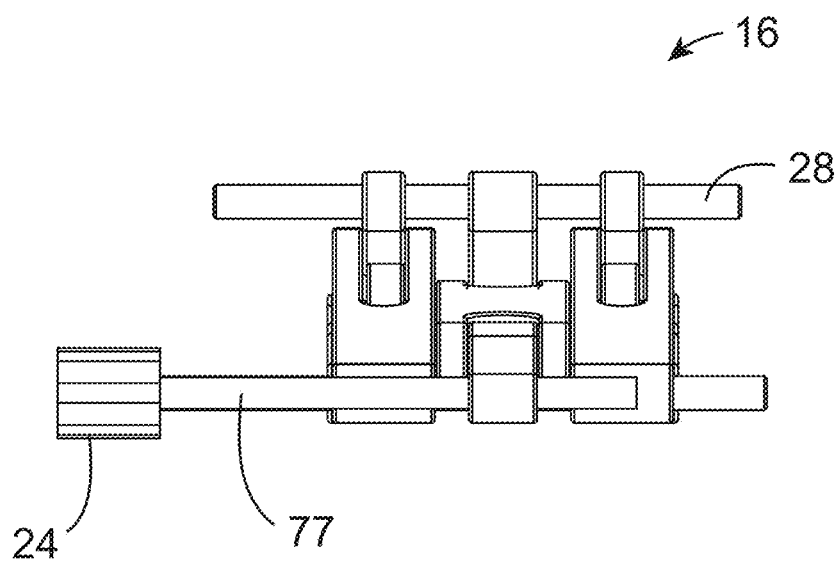
FIG. 12 is an end elevation view of the internal linkage shown in FIG. 9.
Figure 13:
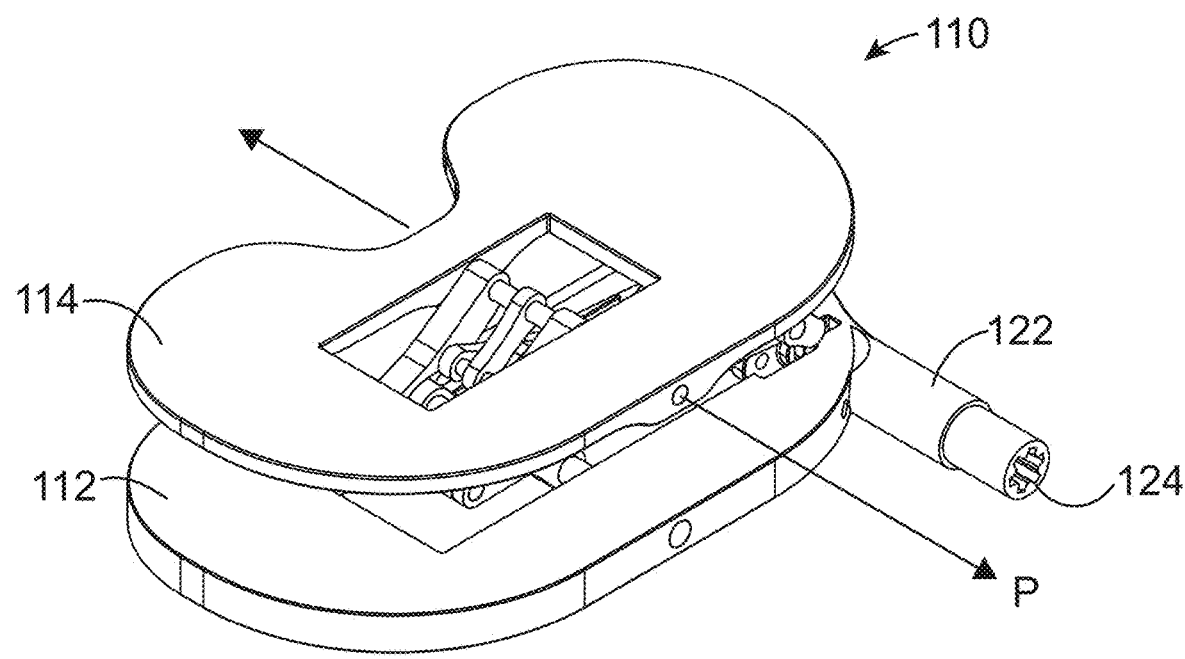
FIG. 13 is a perspective view of an exemplary tensioner-balancer, in an extended position.
Figure 14:
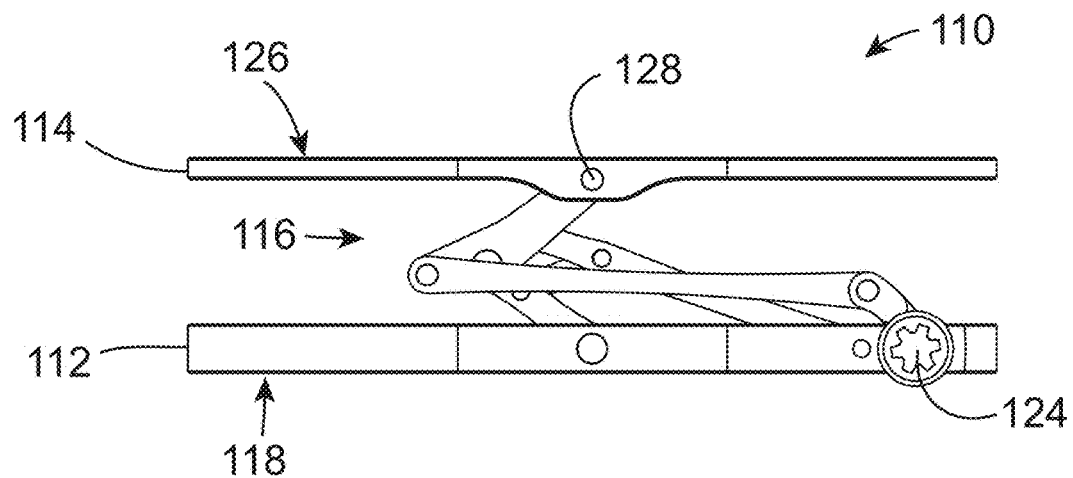
FIG. 14 is a front elevation view of the tensioner-balancer of FIG. 13.
Figure 15:
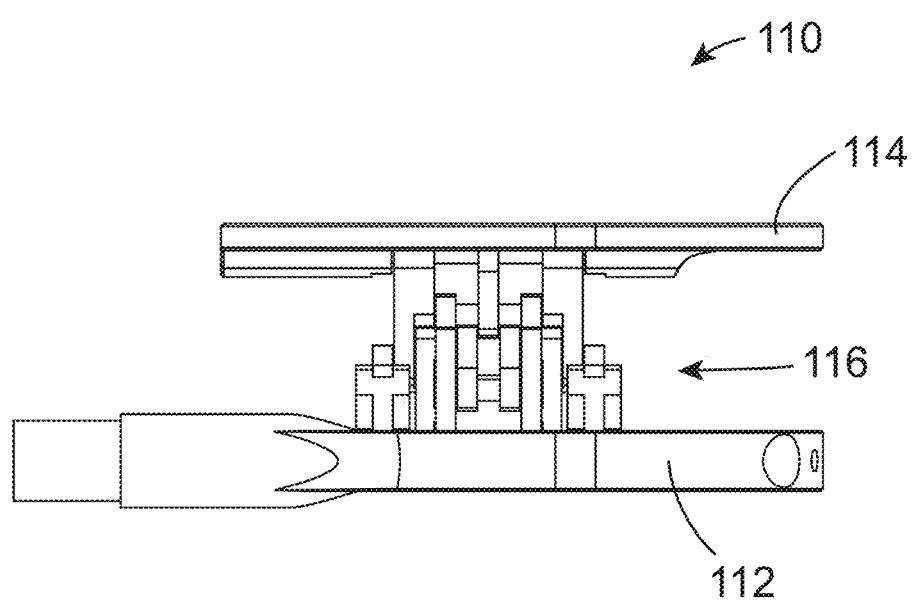
FIG. 15 is a side elevation view of the tensioner-balancer of FIG. 13.
Figure 16:
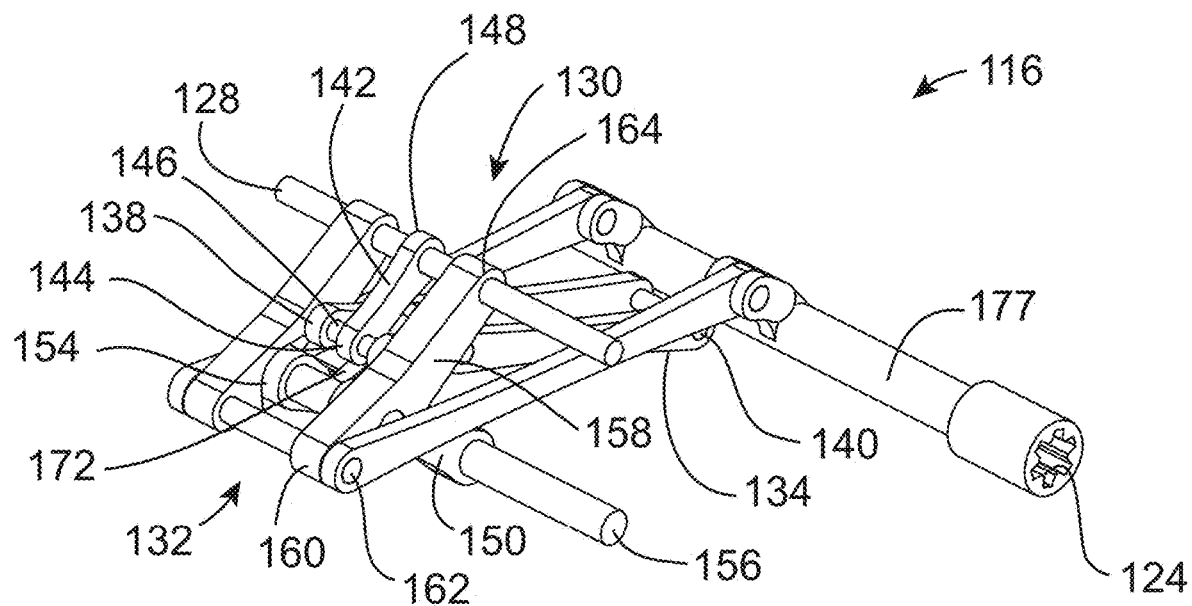
FIG. 16 is a perspective view of the internal linkage of the tensioner-balancer of FIG. 13.

Referring to the drawings wherein identical reference numerals denote the same elements throughout the various views, FIGS. 5-12 depict an exemplary tensioner-balancer 10 which is useful for balancing a gap a human knee joint as part of a total knee arthroscopy. This device may alternatively be referred to as a gap balancer, gap tensioner, distractor, or jack.

Solely for purposes of convenient description, the tensioner-balancer 10 may be described as having a length extending along a lateral-to-medial direction "L", a width extending along an axial direction "A", and a height extending along a vertical direction "H", wherein the lateral direction, the axial direction, and the vertical direction are three mutually perpendicular directions. These directional terms, and similar terms such as "top", "bottom", "upper", "lower" are used merely for convenience in description and do not require a particular orientation of the structures described thereby.

In one aspect, the tensioner-balancer 10 may be described as having the ability to control the movement of one degree of freedom (translation along H) and measure the movement of a second degree of freedom (rotation about A) while constraining or fixing the remaining four degrees of freedom (translation along A and L; rotation about H and L).

The tensioner-balancer 10 comprises a baseplate 12 and a top plate 14 interconnected by a linkage 16. The linkage 16 and the tensioner-balancer 10 are movable between a retracted position in which the top plate 14 lies close to or against the baseplate 12 (FIG. 8), and an extended position (FIG. 6) in which the top plate 14 is spaced away from the baseplate 12. As described in more detail below, a mechanism is provided to actuate the linkage 16 in response to an actuating force in order to separate the baseplate 12 and the top plate 14 in a controllable manner.

The baseplate 12 includes a tibia interface surface 18 which may be planar or may be contoured.

The baseplate 12 includes a tensioner-balancer coupler 22 having a first interface 24. In the illustrated example, the first interface 24 is configured as a splined socket.

The top plate 14 includes a femoral interface surface 26 which may be planar or may be contoured. The top plate 14 is mounted to the linkage 16 in such a manner that it can freely pivot about pivot axis P. An example tilted position of the top plate 14 is shown in phantom lines in FIG. 6 (position labeled 14'). The pivot axis P is parallel to the tibia interface surface 18 and the femur interface surface 26, and in the illustrated orientation is parallel to the axial direction A. In this embodiment, a top pivot pin 28 extends along the pivot axis P and is pivotally coupled to the linkage 16.

The tensioner-balancer 10 may be configured to permit use with the patella in place. This may be achieved by a careful selection of its dimensions and physical configuration. More specifically, an overall width of the tensioner-balancer 10 parallel to direction A in FIG. 5 may be selected to fit behind a patella; and an overall width of the tensioner-balancer 10 parallel to direction L in FIG. 5 may be selected to fit between the medial collateral ligament and the lateral collateral ligament so the device can be inserted into the knee joint. In one example, a distraction height of the tensioner-balancer 10, that is, the distance between the tibia interface surface 18 and the femoral interface surface 26 in the extended position, may lie in a range of about 8 mm to about 20 mm In this embodiment, the linkage 16 is configured as a first toggle linkage 30 connected to the baseplate 12 and the top plate 14, and a second toggle linkage 32 connected to the baseplate 12 and the top plate 14, where the first and second toggle linkages 30, 32 are interconnected with each other.

The first toggle linkage 30 includes a lower link 34 extending between a lower end 36 and an upper end 38. In this embodiment, the upper end 38 of the lower link 34 is forked. The lower end 36 is pivotally connected to the base plate 12 with a first base pin 40 which extends parallel to the pivot axis P. The lower link 34 may be considered a "first link".

The first toggle linkage 30 also includes a pair of upper links 42 which are parallel and spaced-apart from each other along the pivot axis P. Each upper link 42 has a lower end 44 pivotally coupled to the upper end 38 of the lower link 34 by a toggle pin 46, and an upper end 48 pivotally coupled to the top pivot pin 28. The toggle pins 46 extend parallel to the pivot axis P. Collectively, the upper links 42 may be considered a "second link".

The second toggle linkage 32 includes a pair of spaced-apart lower links 50 each extending between a lower end 52 and an upper end 54. The lower ends 52 are pivotally connected to the base plate 12 with a second base pin 56 which extends parallel to the pivot axis P. Collectively, the lower links 50 may be considered a "third link".

The second toggle linkage 32 also includes an upper link 58 which has a lower end 60 pivotally coupled to the upper ends 54 of the lower links 50 by a toggle pin 62 extending parallel to the pivot axis P, and an upper end 64 pivotally coupled to the top pivot pin 28. The upper link 58 may be considered a "fourth link".

A connector linkage 66 includes a pair of spaced-apart connector links 68 each having a first end 70 pivotally connected to the lower link 34 of the first toggle linkage 30, and a second end 72 pivotally connected to one of the lower links 50 of the second toggle linkage 32. The connector links 68 may be considered a "fifth link".

Thus connected, will be understood that movement of the baseplate 12 relative to the top plate 14 will cause interconnected movement of the first and second toggle linkages 30, 32. Or stated another way, movement of either of the first toggle linkage 30 or the second toggle linkage 32 (for example rotation of either of the lower links 34, 50 about the longitudinal axes of their respective base pins 40, 56) will cause movement of the other toggle linkage and the top plate 14 relative to the baseplate 12. In the illustrated example, all of the axes about which the links of the linkage 16 pivot are parallel to each other; in other words, the top pivot pin 28, base pins 40 and 56, and toggle pins 46, 52 are all mutually parallel.

In practical use, one or both of the toggle linkages 30, 32 may be actuated, resulting in movement of the linkage 16 from a retracted position where the baseplate 14 and the top plate 14 are relatively close to or contacting each other, and an extended position with the baseplate 12 is spaced-away from the top plate 14. Throughout this range of motion, the top plate 14 is free to pivot about the pivot axis P.

It will be understood that the toggle linkages 30, 32 may be actuated, for example, by applying a torque causing link rotation about the longitudinal axis of the first base pin 40, by applying a torque causing link rotation about the longitudinal axis of the second base pin 56, by pulling either of the toggle linkages 30, 32, or by pushing either toggle linkage 30, 32.

In the illustrated embodiment, a torque link 74 has a first end 76 pivotally connected to the baseplate 12 by an input shaft 77 which terminates at the first interface 24, and a second end 78 pivotally connected to a transfer bar 80. The transfer bar 80 has a first end 82 pivotally connected to the second end 78 of the torque link 74, and a second end 84 pivotally connected to the second toggle linkage 32. A torque may be applied to the torque link 74 through the first interface 24, resulting in pulling or pushing of the second toggle linkage 32. This arrangement may permit a lower input torque for a given extension force between the baseplate 12 and the top plate 14, as compared to application of torque directly to either of the base pins 40, 56.

By appropriate selection of the lengths of the individual members and the pivot positions, the linkage 16 may be configured such that rotational motion of the lower links 34, 50 results in pure vertical translation in the direction of H or nearly pure translation of the baseplate 12 and top plate 14 relative to each other.

More specifically, the action of the complete linkage 16 is such that the toggle linkages 30, 32 tend to "open" as the mechanism is actuated or stated another way, the angle between the upper links and the respective lower links tends to open or increase as the lower links are rotated from the retracted position to the extended addition. This causes a movement of the upper links along an arc opposite to the arc of the lower links. The two lateral movements (i.e., parallel to direction L) cancel each other, resulting in a net vertical linear movement i.e., parallel to direction H)

In this description, the term "link" refers generally to a substantially rigid element. It will be understood that for any of the first through fifth links described above, an equivalent link may be substituted while maintaining equivalent mechanics of the overall linkage 16. For example, the relationship of which links are forked or paired and which are single or central may be inverted or reversed from this description. In other words, the selection and ordering (front to back) of the linkages and toggles is not critical for the conversion of rotary motion into linear motion.

As an example, FIGS. 13-19 illustrate an alternative tensioner-balancer 110 similar in construction to tensioner-balancer 10 but having a different linkage. The tensioner-balancer 110 comprises a baseplate 112 and a top plate 114 interconnected by a linkage 116. The linkage 116 and the tensioner-balancer 110 are movable between a retracted position in which the top plate 114 lies close to or against the baseplate 112 and an extended position in which the top plate 114 is spaced away from the baseplate 112.

The baseplate 112 includes a tibia interface surface 118 and a tensioner-balancer coupler 122 having a first interface 124 such as a splined socket.

The top plate 114 includes a femoral interface surface 126 and is mounted to the linkage 116 in such a manner that it can freely pivot about pivot axis P. In this embodiment, a top pivot pin 128 extends along the pivot axis P and is pivotally coupled to the linkage 116.

In this embodiment, the linkage 116 is configured as a first toggle linkage 130 connected to the baseplate 112 and the top plate 114, and a second toggle linkage 132 connected to the baseplate 112 and the top plate 114, where the first and second toggle linkages 130, 132 are interconnected with each other.

The first toggle linkage 130 includes a pair of lower links 134 extending between lower ends 136 and upper ends 138. The lower ends 136 are pivotally connected to the base plate 112 with a first base pin 140 which extends parallel to the pivot axis P.

The first toggle linkage 130 also includes an upper link 142 which has a lower end 144 pivotally coupled to the upper ends 138 of the lower links 134 by a toggle pin 146, and an upper end 148 pivotally coupled to the top pivot pin 128. The toggle pin 146 extends parallel to the pivot axis P.

The second toggle linkage 132 includes a pair of spaced-apart lower links 150 each extending between a lower end 152 and an upper end 154. The lower ends 152 are pivotally connected to the base plate 112 with a second base pin 156 which extends parallel to the pivot axis P.

The second toggle linkage 132 also includes a pair of spaced-apart upper links 158 which each have a lower end 160 and an upper end 164. A middle portion of each upper link 158 is pivotally coupled to the upper end 154 of the respective lower link 150 by a toggle pin 162 extending parallel to the pivot axis P. The upper end 164 of each upper link 158 is pivotally coupled to the top pivot pin 128.

A connector linkage 166 includes a pair of spaced-apart connector links 168 each having a first end 170 pivotally connected to one of the lower links 134 of the first toggle linkage 130, and a second end 172 pivotally connected to one of the lower links 150 of the second toggle linkage 132.

Thus connected, will be understood that movement of the baseplate 112 relative to the top plate 114 will cause interconnected movement of the first and second toggle linkages 130, 132. Or stated another way, movement of either of the first toggle linkage 130 or the second toggle linkage 132 (for example rotation of either of the lower links 134, 150 about their respective base pins 140, 156) will cause movement of the other toggle linkage and the top plate 114 relative to the baseplate 1112.

In practical use, one or both of the toggle linkages 130, 132 may be actuated, resulting in movement of the linkage 116 from a retracted position where the baseplate 114 and the top plate 114 are relatively close to or contacting each other, and an extended position with the baseplate 112 is spaced-away from the top plate 114. Throughout this range of motion, the top plate 114 is free to pivot about the pivot axis P.

In the illustrated embodiment, a pair of spaced-apart torque links 174 have first ends 176 pivotally connected to the baseplate 112 by an input shaft 177 which terminates at the first interface 124, and second ends 178 pivotally connected to first and second transfer bars 180. Each of the transfer bars 180 has a first end 182 pivotally connected to the second end 178 of the corresponding torque link 174, and a second end 184 pivotally connected to the second toggle linkage 132. A torque may be applied to the torque links 174 via the first interface 124 and input shaft 177, resulting in pulling or pushing of the second toggle linkage 132.

FIGS. 20-26 illustrate an alternative tensioner-balancer 210 similar in construction to tensioner-balancer 10 but having yet another different linkage configuration The tensioner-balancer 210 comprises a baseplate 212 and a top plate 214 interconnected by a linkage 216. The linkage 216 and the tensioner-balancer 210 are movable between a retracted position in which the top plate 214 lies close to or against the baseplate 212 and an extended position in which the top plate 214 is spaced away from the baseplate 212.

The baseplate 212 includes a tibia interface surface 218 and a tensioner-balancer coupler 222 having a first interface 224 such as a splined socket.

The top plate 214 includes a femoral interface surface 226 and is mounted to the linkage 216 in such a manner that it can freely pivot about pivot axis P. In this embodiment, a top pivot pin 228 extends along the pivot axis P and is pivotally coupled to the linkage 216.

In this embodiment, the linkage 216 is configured as a first toggle linkage 230 connected to the baseplate 212 and the top plate 214, and a second toggle linkage 232 connected to the baseplate 212 and the top plate 214. In contrast to the linkages 16, 116 described above, the linkage 216 is laterally symmetrical.

The first toggle linkage 230 includes a pair of spaced-apart lower links 234 extending between lower ends 236 and upper ends 238. The lower ends 236 are pivotally connected to the base plate 212 with a first base pin 240 which extends parallel to the pivot axis P. The lower links 234 are fixed relative to the first base pin 240, and the lower links 234 and the first base pin 240 rotate in unison relative to the baseplate 212. The first base pin 240 also functions as an input shaft and terminates at a first interface 224.

The first toggle linkage 230 also includes a pair of upper links 242 which are parallel and spaced-apart from each other along the pivot axis P. Each upper link 242 has a lower end 244 pivotally coupled to the upper end 238 of the respective lower link 234 by a toggle pin 246, and an upper end 248 pivotally coupled to the top pivot pin 228. The toggle pins 246 extend parallel to the pivot axis P.

The second toggle linkage 232 includes a pair of spaced-apart lower links 250 each extending between a lower end 252 and an upper end 254. The lower ends 252 are pivotally connected to the base plate 212 with a second base pin 256 which extends parallel to the pivot axis P.

The second toggle linkage 232 also includes a pair of spaced-apart upper links 258 each having a lower end 260 pivotally coupled to the upper ends 254 of the respective lower link 250 by a toggle pin 262 extending parallel to the pivot axis P, and an upper end 264 pivotally coupled to the top pivot pin 228.

The first and second base pins 240, 256 are interconnected with each other to synchronize the movement of the two toggle linkages 230, 232. A connector linkage 266 includes a connector link 268 having a first end 270 connected to the first base pin 240 by a crank arm (not separately labeled), and a second end 272 pivotally connected to the second toggle linkage 232 by a crank arm (not separately labeled)

Thus connected, will be understood that movement of the baseplate 212 relative to the top plate 214 will cause interconnected movement of the first and second toggle linkages 230, 232. Or stated another way, movement of either of the first toggle linkage 230 or the second toggle linkage 232 (for example rotation of either of the lower links 234, 250 about the longitudinal axes of their respective base pins 240, 256) will cause movement of the other toggle linkage and the top plate 214 relative to the baseplate 212.

In practical use, rotation of the first base pin 240 will result in movement of the linkage 216 from a retracted position where the baseplate 212 and the top plate 214 are relatively close to or contacting each other, and an extended position with the baseplate 212 is spaced-away from the top plate 214. Throughout this range of motion, the top plate 214 is free to pivot about the pivot axis P.

Optionally, the linkage/toggle assembly can be symmetrically reflected in the direction of "L" or "A" (FIG. 5) resulting in two devices that are symmetrical for either side of the knee. Alternatively the input shaft 24 alone can be reflected in the direction of "A" (this would require torque applied in the opposite direction to drive the linkage assembly upwards). Furthermore, optionally, while not shown, a device could be constructed with one baseplate and two spaced-apart top plates, one for each femoral condyle. A separate linkage 16 as described above may be provided for each top plate. This would allow the separate top plates to be driven with independent torques or interconnected torques.

Each of the linkages described herein has predetermined kinematic properties, or stated another way, the ratio of displacement of the top plate 14 to input displacement is known and can be plotted a graph, for the entire range of motion. The ratio of input torque to output distraction force is also known continuously throughout the device range of motion which is useful in determining the exact distraction force being applied at any given height.

Figure 27:
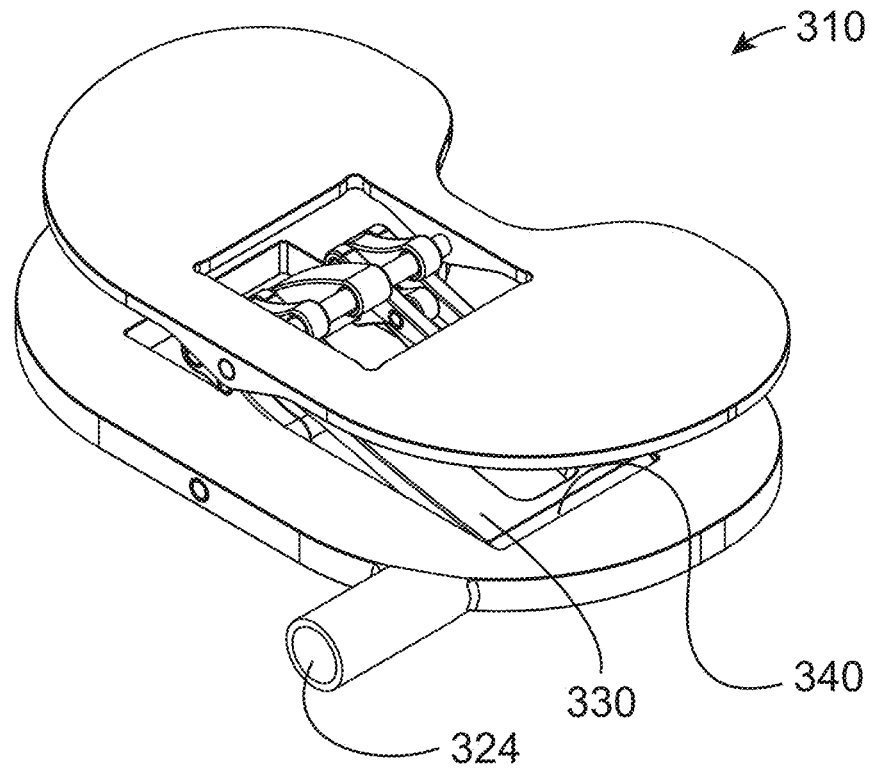
FIG. 27 is a perspective view of an alternative embodiment of a tensioner-balancer.
Figure 28:
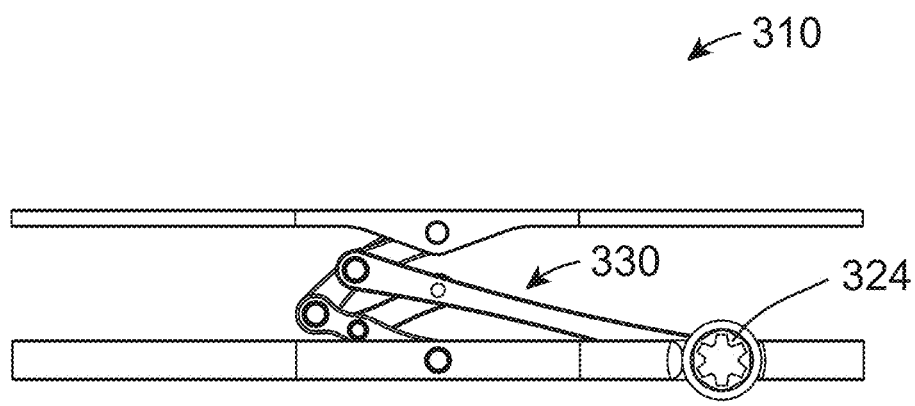
FIG. 28 is a front elevation view of the tensioner-balancer of FIG. 27.

FIGS. 27 and 28 illustrate an alternative tensioner-balancer 310 similar in overall construction to the tensioner-balancer 10 described above. Elements of the tensioner-balancer 310 not explicitly described may be considered to be identical to corresponding components of the tensioner-balancer 10. The tensioner-balancer 310 differs from the tensioner-balancer 10 only in that the torque link and transfer bar are eliminated. In use, actuating torque would be applied directly to the first toggle linkage 330 through a first interface 324, for example a splined socket connected directly to the first base pin 340.

Figure 29:
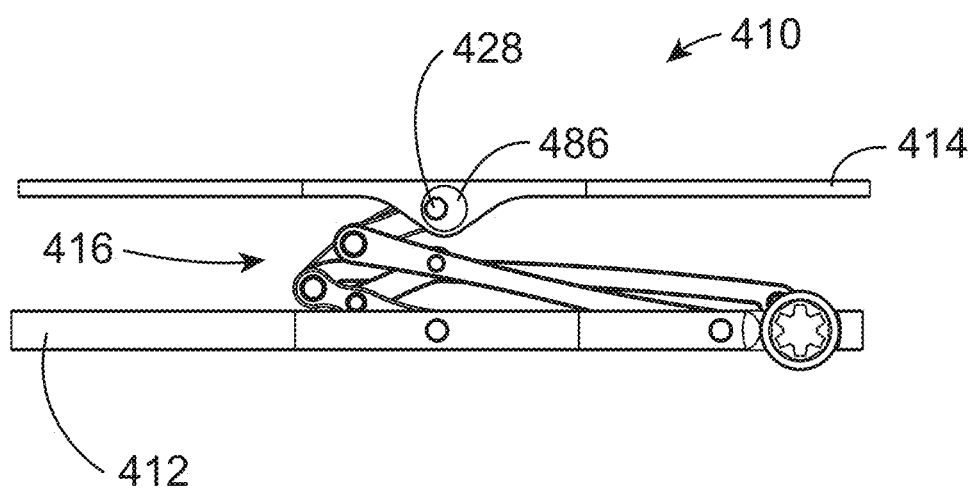
FIG. 29 is a front elevation view of an alternative embodiment of a tensioner-balancer.

FIG. 29 illustrates an alternative tensioner-balancer 410 similar in overall construction to the tensioner-balancer 10 described above. Elements of the tensioner-balancer 310 not explicitly described may be considered to be identical to corresponding components of the tensioner-balancer 10. The tensioner-balancer 410 differs from the tensioner-balancer 10 in that the top pivot pin 428 is mounted to the top plate 414 via an eccentric bushing 486. Using an appropriate instrument (not shown), the eccentric bushing 486 may be rotated within the top plate 414 independent of the operation of the linkage 416 or the pivoting motion of the top plate 414. Rotation of the eccentric bushing 486 will cause relative movement of the top plate 414 and the top pivot pin 428. This function may be used to accommodate variations in a specific patient's anatomy. Stated another way, the top plate 414 may be laterally offset from the baseplate 412. Specifically, this function may be used to intentionally shift the center of mass of the load on the top plate 414 medially or laterally.

Figure 30:
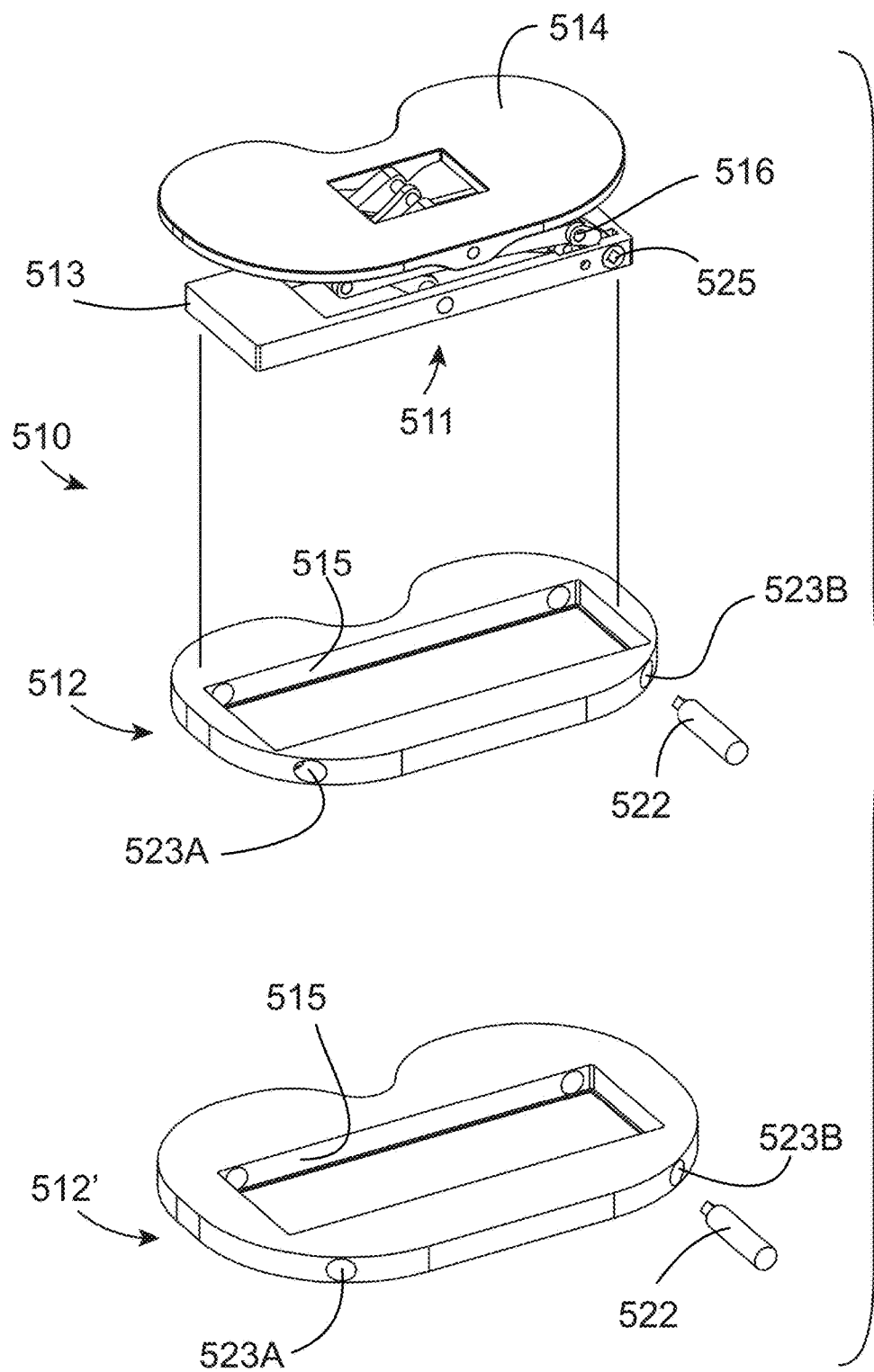
FIG. 30 is an exploded perspective view of an exemplary modular tensioner-balancer, in an extended position.

FIG. 30 illustrates an alternative tensioner-balancer 510 similar in overall construction to the tensioner-balancer 10 described above but having a modular construction. The tensioner-balancer 510 comprises a frame 511 and a top plate 514 interconnected by a linkage 516. The linkage 516 and the tensioner-balancer 510 are movable between a retracted position in which the top plate 514 lies close to or against the frame 511 and an extended position in which the top plate 514 is spaced away from the baseplate 512. The frame 511 has an interface surface 513 formed in a convenient shape such as the illustrated rectangle.

The frame 511 may be received in one or more baseplates 512, 512'. These my be of different external shapes or sizes to accommodate different patients, but each has a common interface surface 515 which in this example is a rectangular opening. The interface surface 513 of the frame 511 fits into the interface surface 515 and may be retained by means such as a friction fit or mechanical fasteners (not shown). The assembly is completed by attaching a tensioner-balancer coupler 522 to the baseplate 512. The baseplate 512 may be provided with mounting holes (523A, 523B) on both left and right sides so that the coupler 522 can be attached on either side and connected to a socket 525 of the frame 511. To reverse the frame 511, the top plate 514 would be detached from the linkage 516, rotated 180 degrees, and re-attached to the linkage 516. This configuration permits a single linkage 516 to be used for either a left or right knee joint in multiple sizes.

Figure 31:
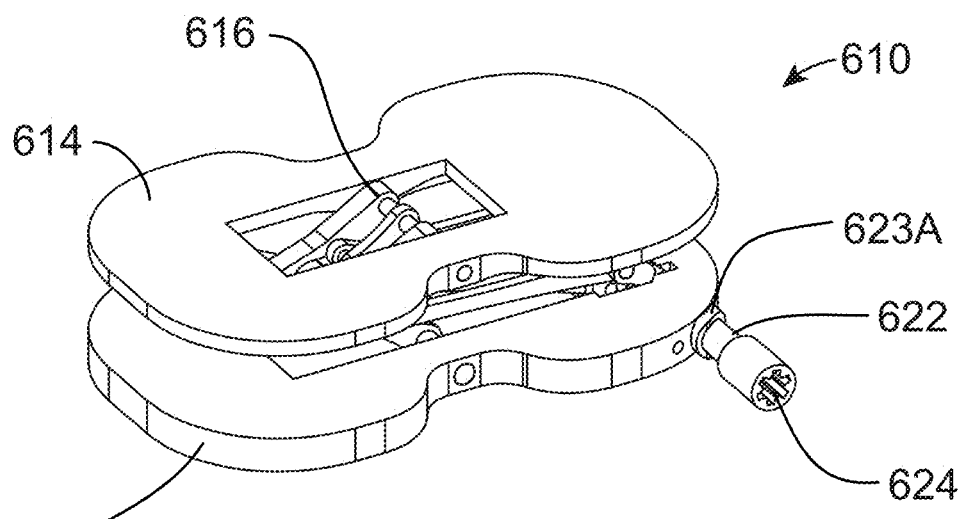
FIG. 31 is a front perspective view of an exemplary symmetrical tensioner-balancer, in an extended position.
Figure 32:
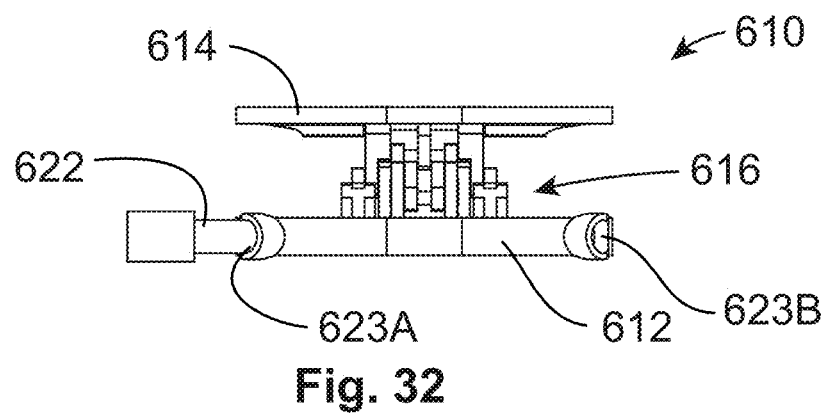
FIG. 32 is a side elevation view of the tensioner-balancer of FIG. 31.
Figure 33:
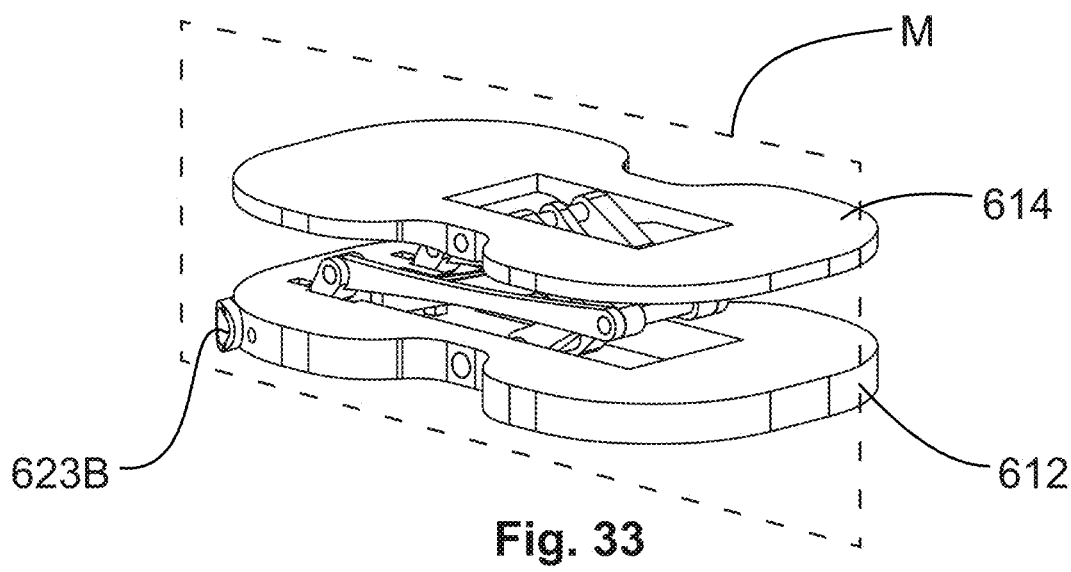
FIG. 33 is a rear perspective view of tensioner-balancer of FIG. 31.

FIGS. 31-33 illustrate an alternative tensioner-balancer 610 similar in overall construction to the tensioner-balancer 10 described above but having an anterior-posterior symmetric construction. The tensioner-balancer 610 comprises a baseplate 612 and a top plate 614 interconnected by a linkage 616. The linkage 616 and the tensioner-balancer 610 are movable between a retracted position in which the top plate 614 lies close to or against the baseplate 612 and an extended position in which the top plate 614 is spaced away from the baseplate 614. The baseplate 612 and the top plate 614 are both symmetrical about a mid-plane "M" shown in FIG. 33. Thus configured, the tensioner-balancer 610 can be rotated 180 degrees and used in either a right or left knee joint. To accommodate this function, the baseplate 612 is provided with a pair of opposed mounting holes 623A, 623B respectively. A coupler 622 having a first interface 624 is inserted into the appropriate one of the mounting holes, depending on which knee the tensioner-balancer 610 is to be used for. Alternatively, the mounting holes 623A, 623B may be configured with appropriate drive instrument connection features such as splines or bayonet connections, so that assembly of coupler 622 is not required.

Figure 34:
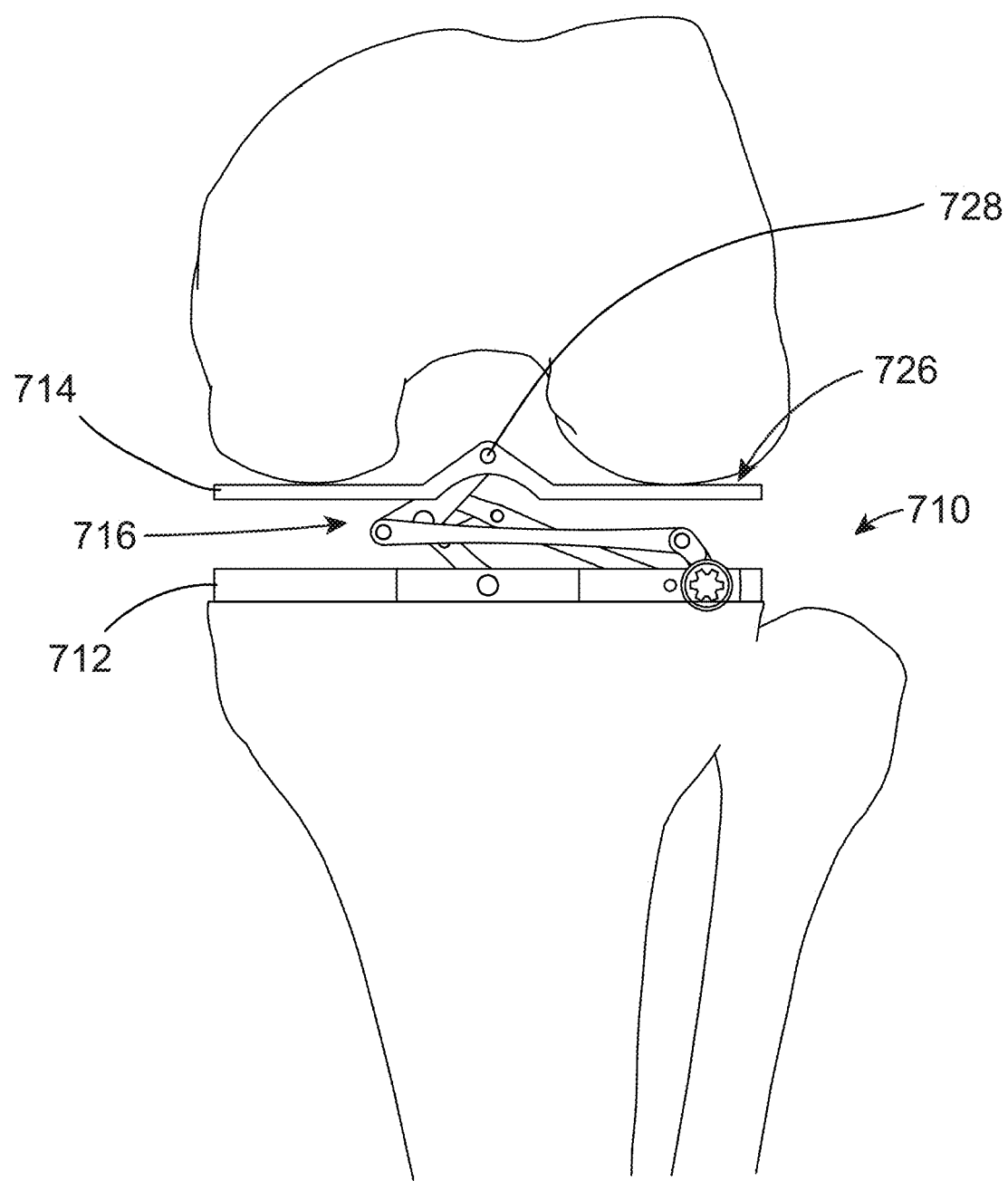
FIG. 34 is a front elevation view of an alternative embodiment of a tensioner-balancer, incorporating a "gull wing" shape.

FIG. 34 illustrates an alternative tensioner-balancer 710 similar in overall construction to the tensioner-balancer 10 described above. The tensioner-balancer 710 comprises a baseplate 712 and a top plate 714 interconnected by a linkage 716. The linkage 716 and the tensioner-balancer 710 are movable between a retracted position in which the top plate 714 lies close to or against the baseplate 712 and an extended position in which the top plate 714 is spaced away from the baseplate 714. The top plate 714 has an "inverted gull-wing" configuration in which the top pivot pin 728 is positioned above the femoral interface surface 726, or stated another way, the femoral interface surface 726 is between the top pivot pin 728 and the linkage 716. This configuration may permit the tensioner-balancer 710 to have reduced overall thickness in the retracted position while still providing physical space for the linkage 716.

Figure 35:
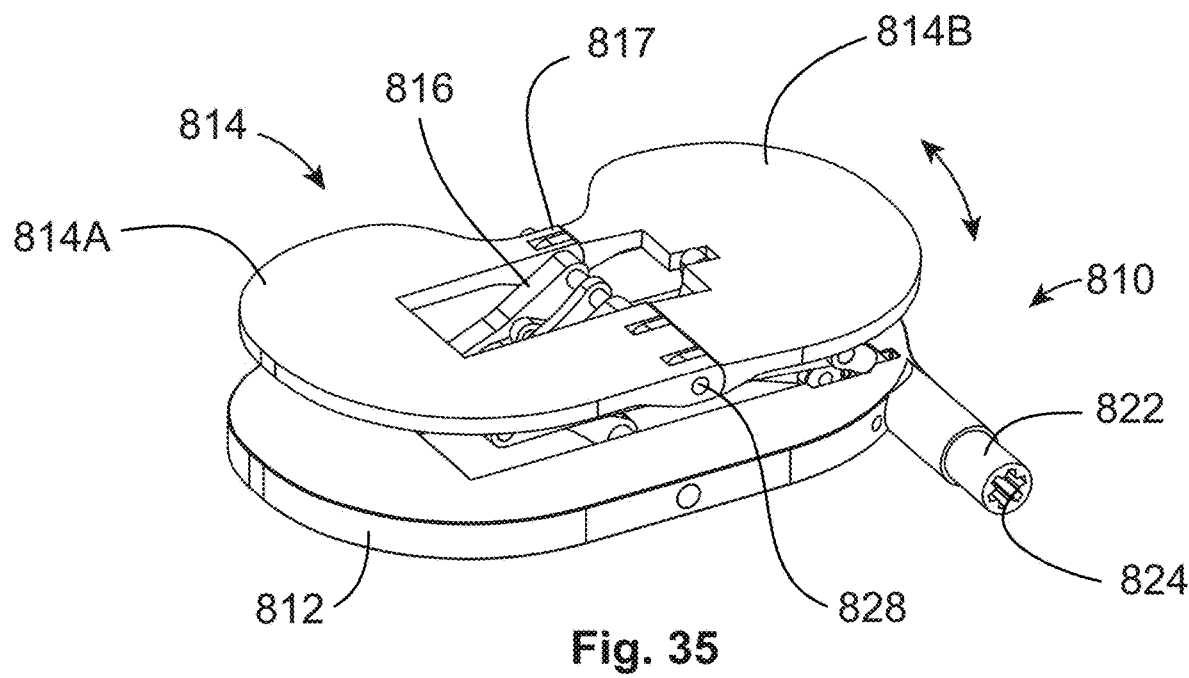
FIG. 35 is a perspective view of an alternative embodiment of a tensioner-balancer, incorporating a hinged top plate.
Figure 36:
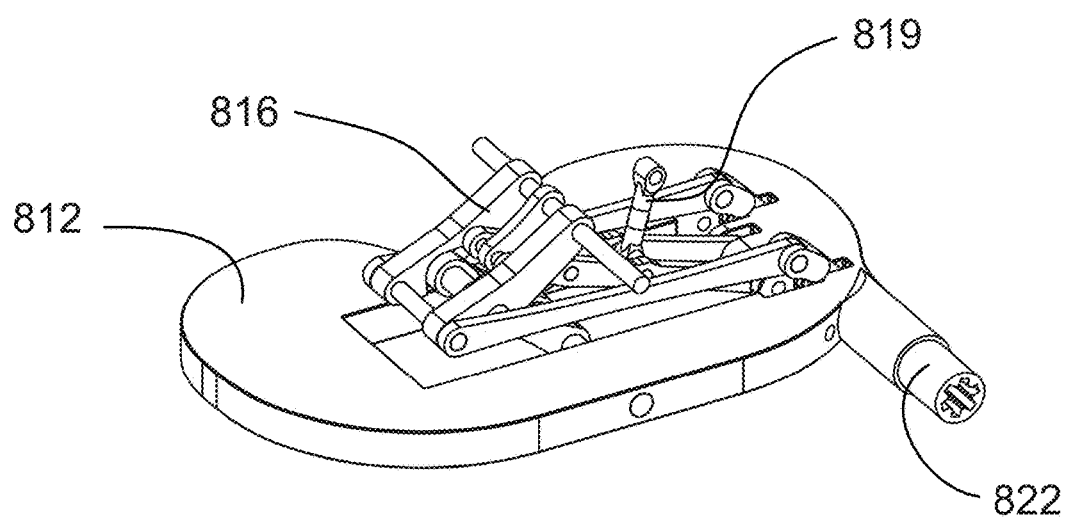
FIG. 36 is another view of the tensioner-balancer of FIG. 35, with the top plate removed.

FIGS. 35 and 36 illustrate an alternative tensioner-balancer 810 similar in overall construction to the tensioner-balancer 10 described above but having an hinged top plate. The tensioner-balancer 810 comprises a baseplate 812 and a top plate 814 interconnected by a linkage 816. The linkage 816 and the tensioner-balancer 910 are movable between a retracted position in which the top plate 814 lies close to or against the baseplate 812 and an extended position in which the top plate 814 is spaced away from the baseplate 814. A coupler 822 having a first interface 824 extends from the baseplate 812. The top plate 814 comprises left and right sections 814A, 814B respectively, joined at a hinge 817 that pivots about the top pivot pin 828. Thus configured, the right section 814A can pivot up or down relative to the left section 814A. The independent pivoting movement of the right section 814B may be controlled by a pivot linkage 819 mounted to the baseplate 819 and operated independently of the link age 816. Pivot linkage 819 may be mechanically or electronically controlled and/or measured. Pivot linkage 819 would also be suitable for being connected to a non-hinged top plate, to provide a capability of controlled top plate tilt.

Figure 37:
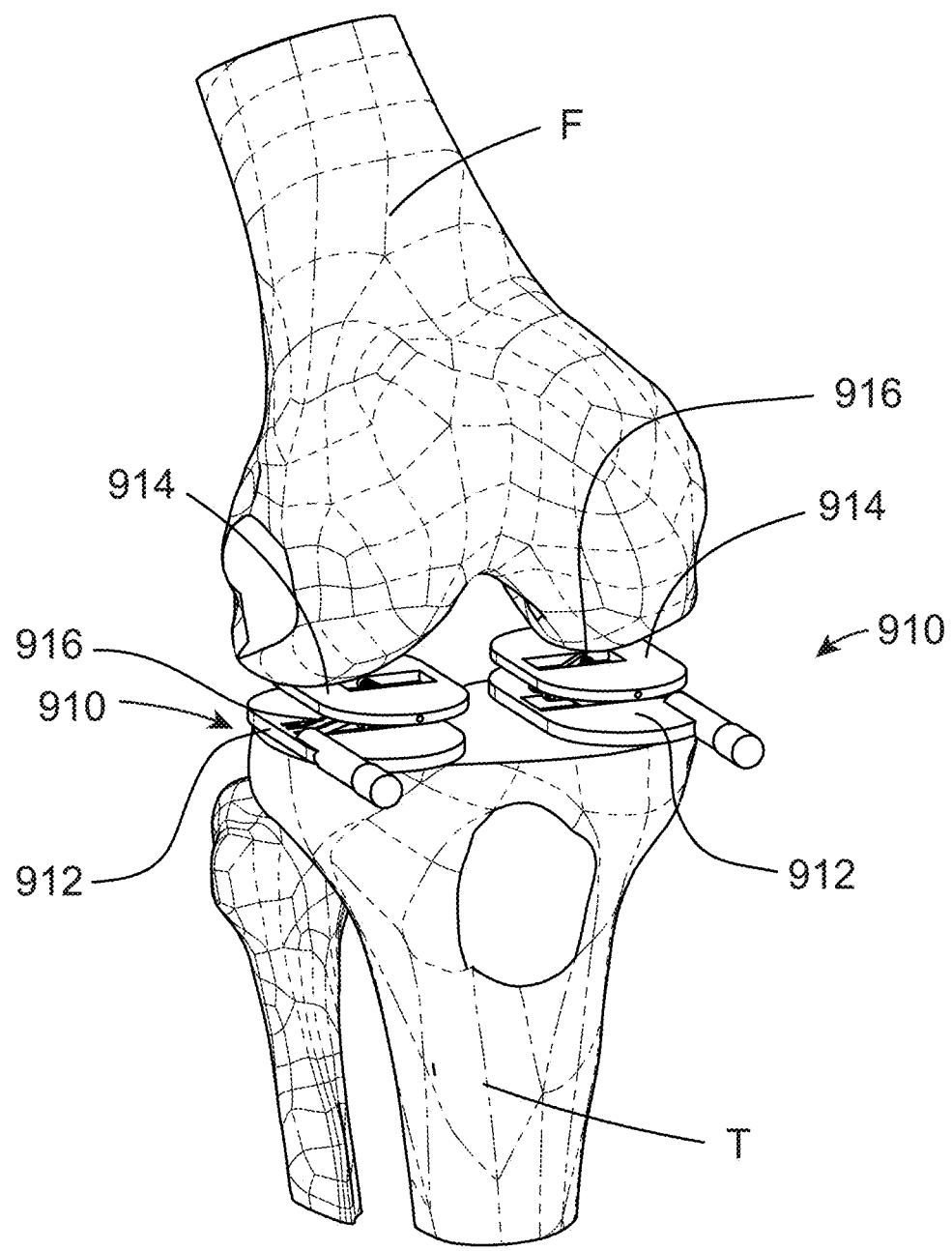
FIG. 37 is a perspective view of a human knee joint showing a pair of tensioner-balancers.
Figure 38:
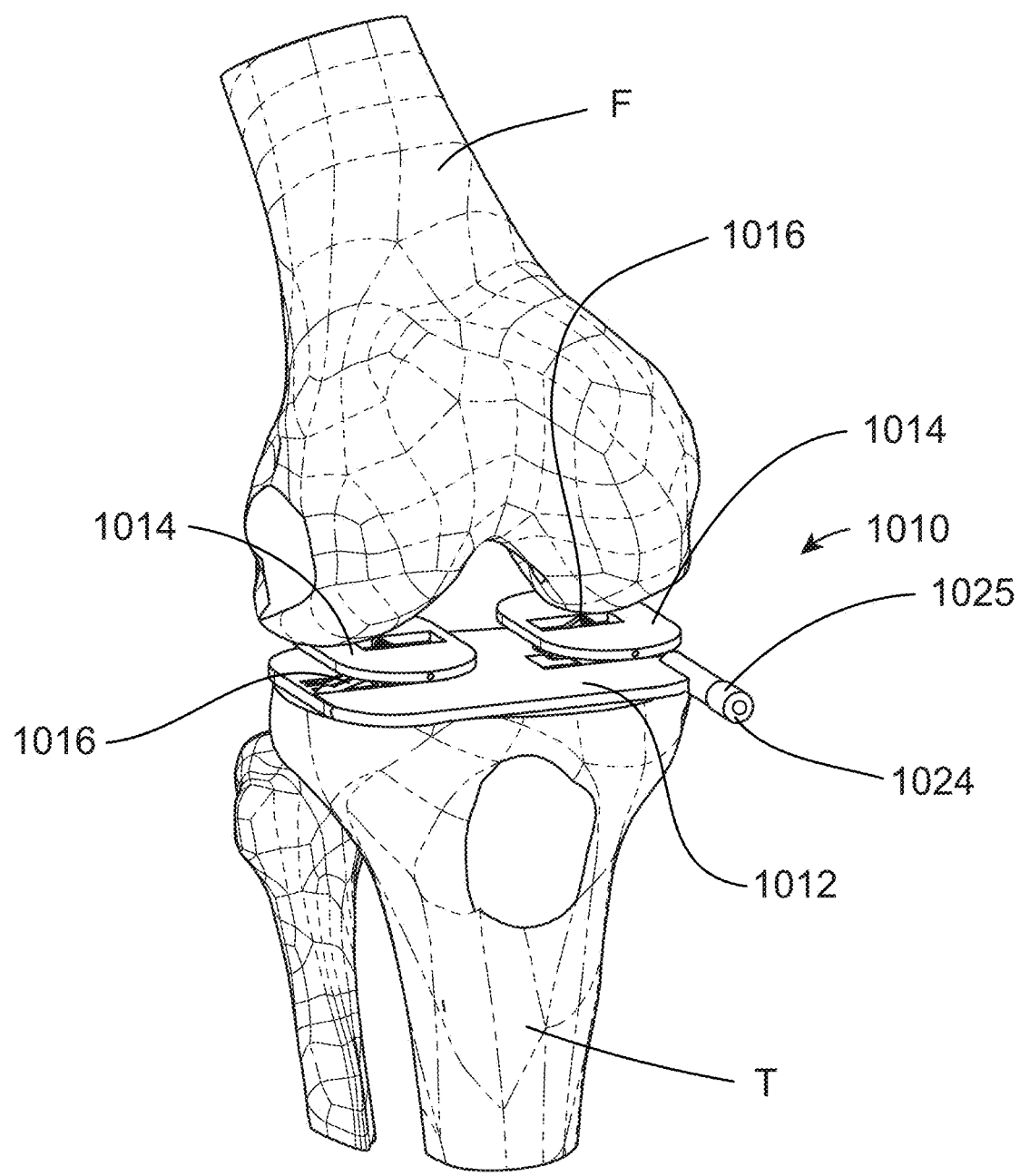
FIG. 38 is a perspective view of a human knee joint showing a double top plate, single base plate tensioner-balancer.
Figure 39:
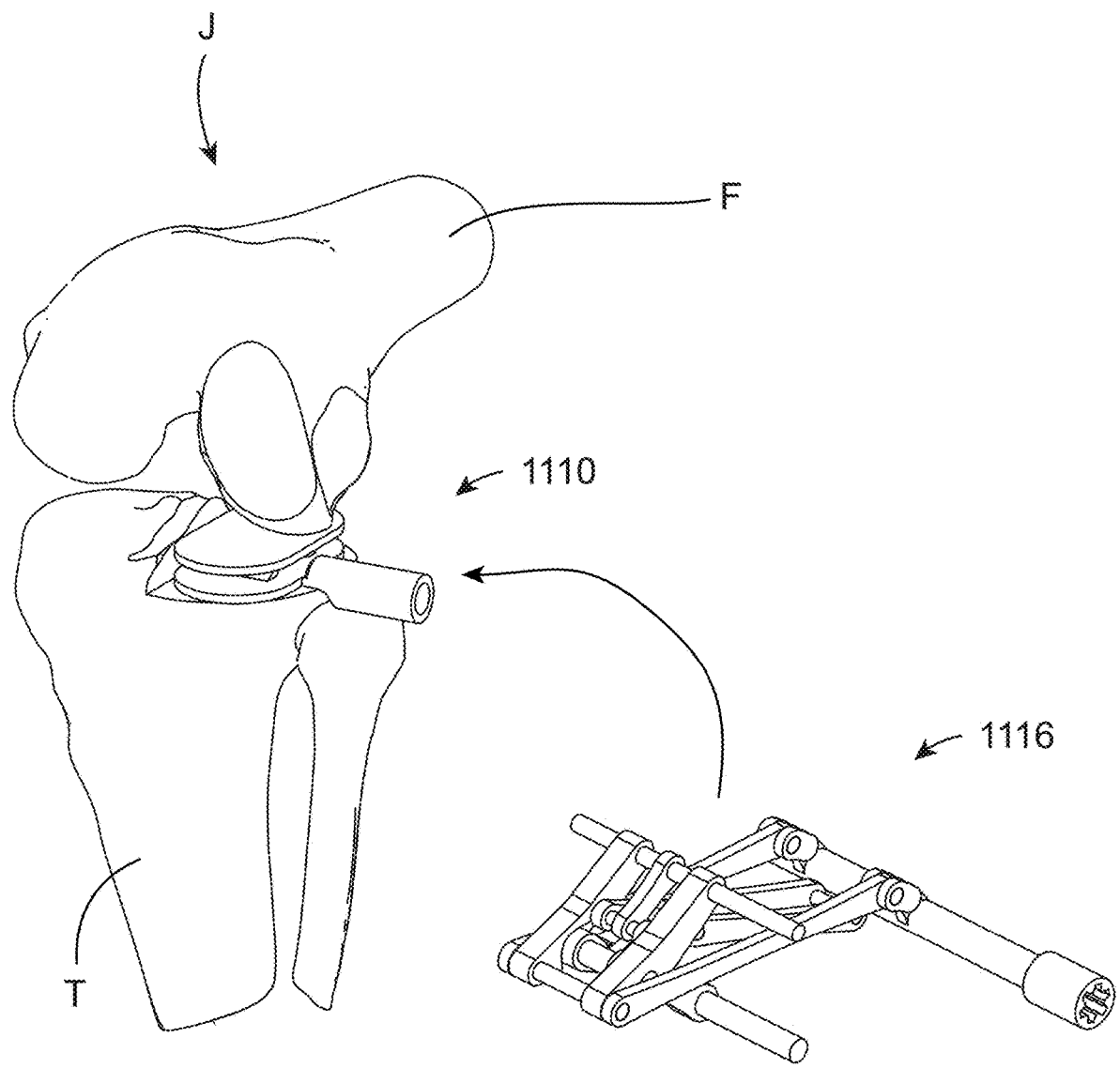
FIG. 39 is a perspective view of a human knee joint showing a single tensioner-balancer under the lateral condyle.

The tensioner-balancer may be for a total knee as described above. Alternatively, as depicted in FIG. 37, two individual smaller-scale tensioner-balancers 910 each having a separate baseplate 912, linkage 916, and top plate 914 may be used for the medial and lateral compartments, respectively. Alternatively, as depicted in FIG. 38, a tensioner-balancer 1010 having a single baseplate 1012, and two separate top plates 1014 each with its own linkage 1016 may be used for the medial and lateral compartments, respectively. In this embodiment, the tensioner-balancer 1010 may include two separate interfaces such as the illustrated co-axial interfaces 1024, 1025, permitting the medial and lateral linkages to be actuated independently. Alternatively, a single interface may be provided which drives the medial or lateral linkage, and the other linkage would be driven by a spring element interconnection to the directly-driven linkage. Alternatively, the arthroplasty may be uni-compartmental. In that case, one smaller-scale tensioner-balancer 1110 may be used for either the medial or lateral compartment. Optionally, by suitable orientation of the linkage 1116 the tensioner-balancer 1110 may be configured to permit approach of an instrument (not shown) from the medial or lateral aspect of the joint J as opposed to the anterior aspect.

Any of the tensioner-balancer embodiments described herein may be supplied with an appropriate combination of transducers to detect physical properties such as force, tilt angle, and/or applied load and generate a signal representative thereof. For example, the tensioner-balancer may be provided with sensors operable to detect the magnitude of extension (i.e. "gap height"), the angle of the top plate about the pivot axis P (i.e. varus/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers.

Figure 40:
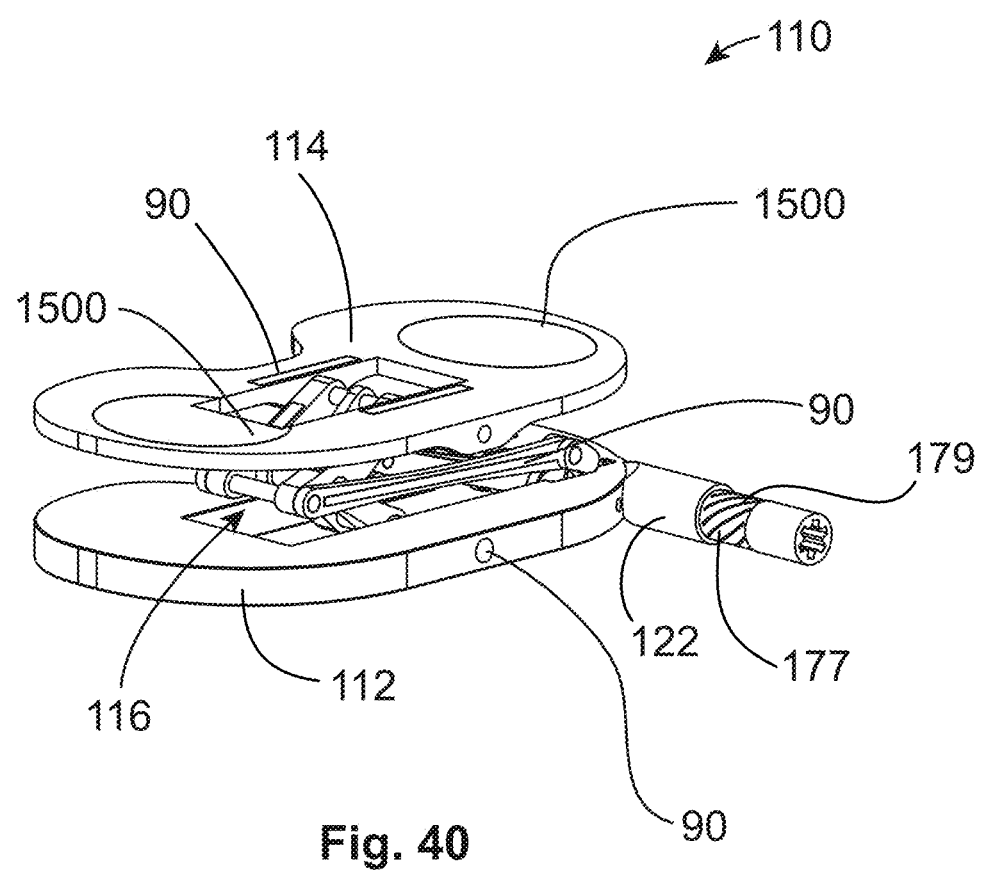
FIG. 40 is a perspective view of a tensioner-balancer incorporating sensors thereon.
Figure 41:
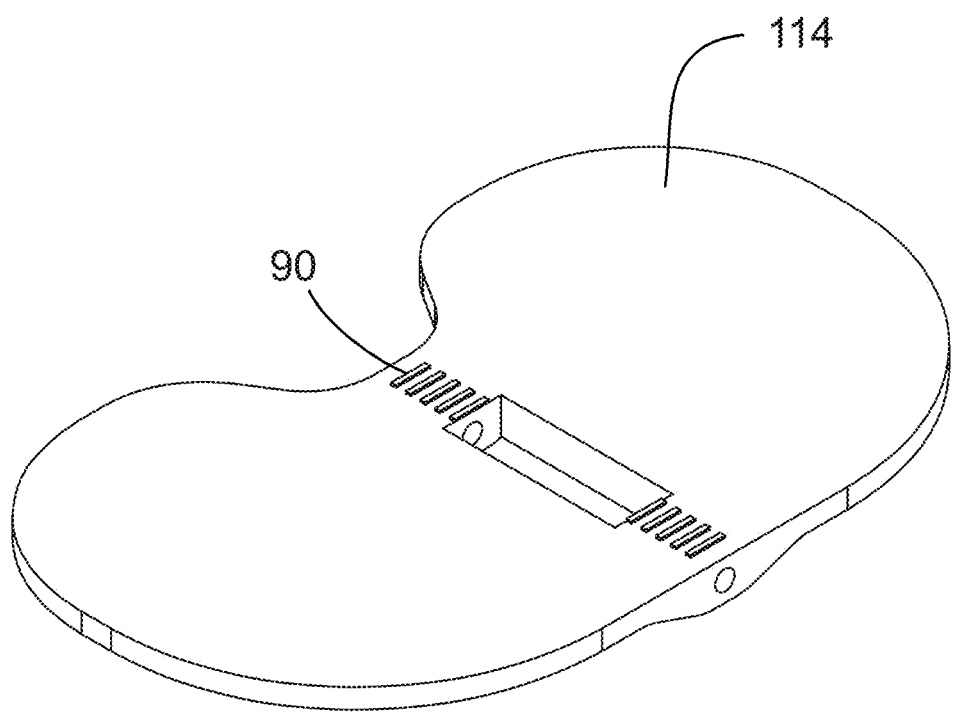
FIG. 41 is a perspective view of a tensioner-balancer top plate, incorporating an array of strain gages.
Figure 42:
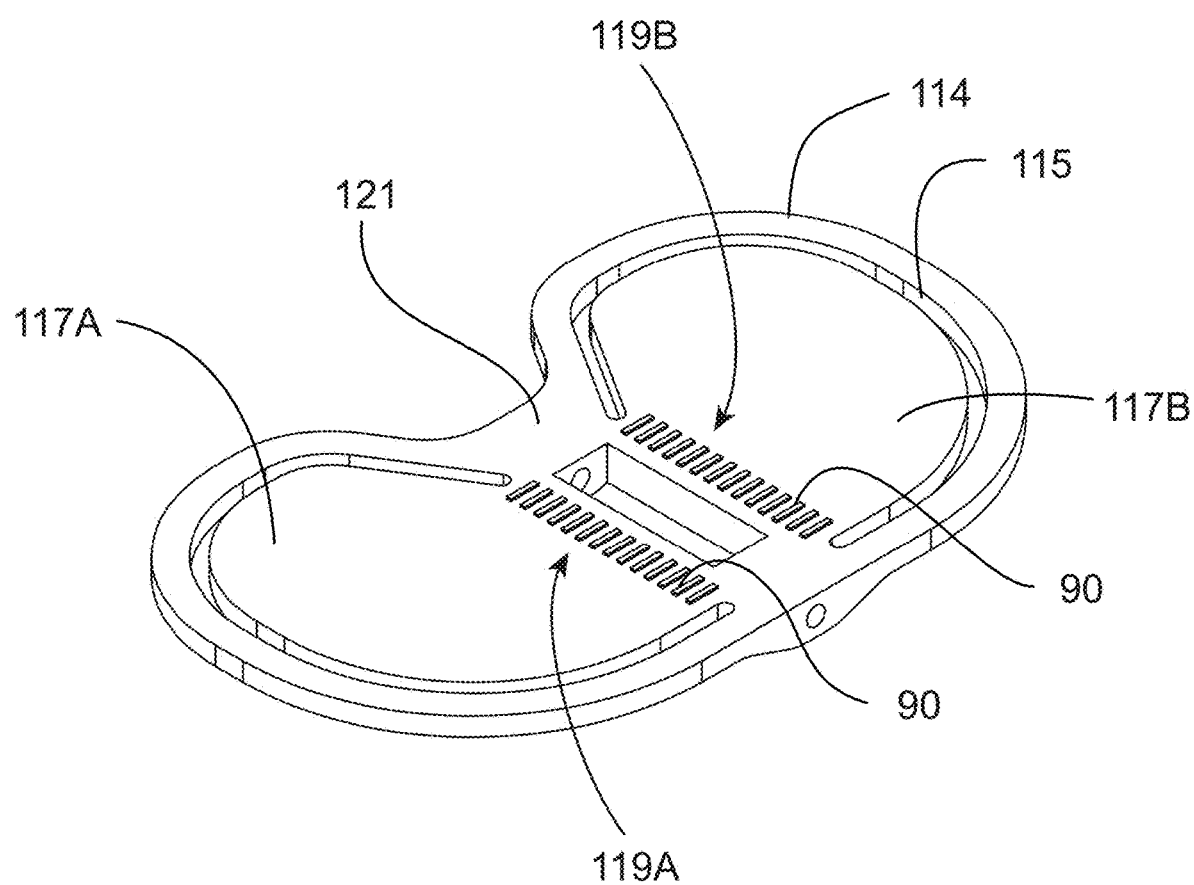
FIG. 42 is a perspective view of a tensioner-balancer top plate, incorporating sensors and flexible portions.

In the example as shown in FIG. 40, one or more strain gages 90 are mounted to the top plate 114 of a tensioner-balancer 110. It will be understood that bending stresses measured by the strain gages 90 can be related to the applied force in the extension direction ("distraction load") through appropriate computations. Pressure applied to pads 1500 on the medial and lateral sides can measure the load on the medial and lateral femoral condyle, respectively, independently. FIG. 41 illustrates a variation in which a plurality of strain gages 90 are mounted to the top plate 114 in a fore-aft row. FIG. 42 illustrates a variation in which the top plate 114 includes grooves 115 which define lateral and medial cantilevered pads 117A, 117B respectively. A plurality of strain gages 90 are mounted to the top plate 114 in a first fore-aft row 119A at the intersection between the lateral pad 117A and the central portion 121 of the top plate 114. A plurality of strain gages 90 are mounted to the top plate 114 in a second fore-aft row 119B at the intersection between the medial pad 117B and the central portion 121 of the top plate 114.

Figure 43:
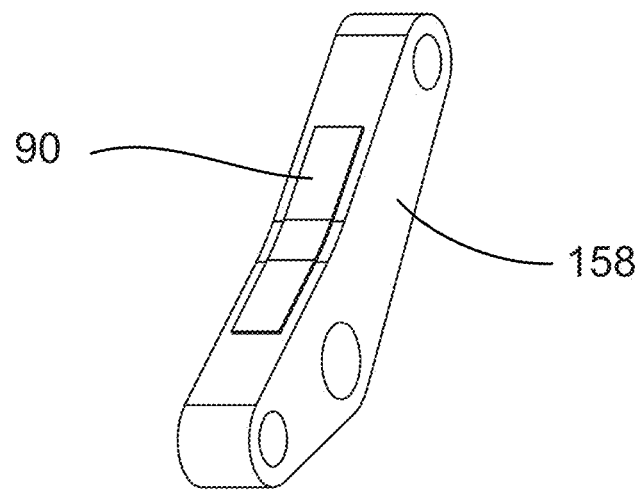
FIG. 43 is a perspective view of a linkage, incorporating sensors.
Figure 44:
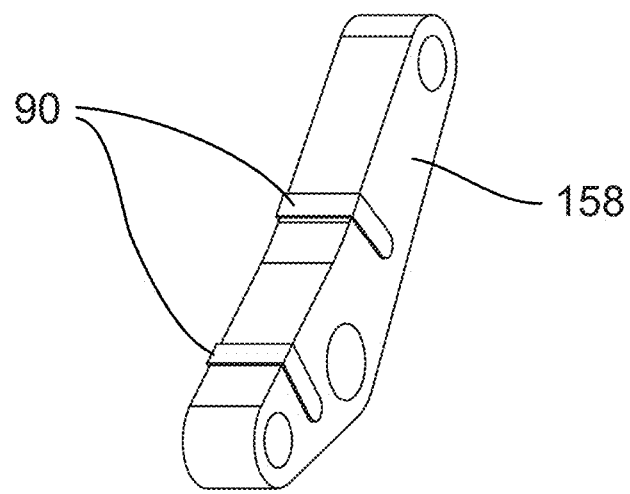
FIG. 44 is a perspective view of a linkage, incorporating sensors.

FIGS. 43 and 44 illustrate links 158 of the linkage 116 having strain gages 90 incorporated therein.

Optionally, the tensioner-balancer 110 may incorporate means for measuring a force input. In the example shown in FIG. 40, the coupler 122 includes an input shaft 177. The input shaft 177 includes a sensor 179 such as a strain gage. The sensor 179 produces a signal representative of the torque applied to the input shaft 177, for example using one of the instruments described below. The sensor 179 may be connected to an electronic receiving device as described elsewhere herein by a wired or wireless connection.

Figure 45:
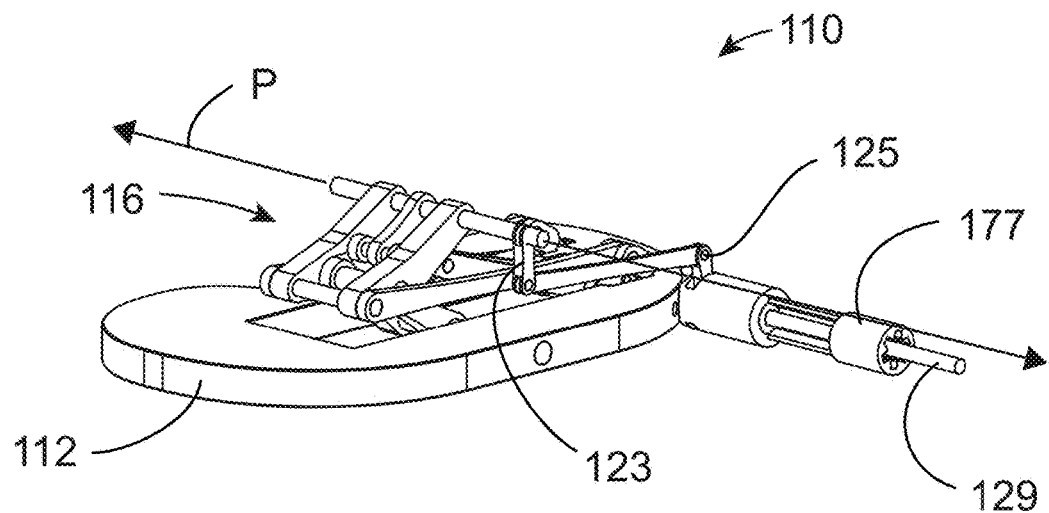
FIG. 45 is a perspective view of a tensioner-balancer incorporating a measurement linkage, with a top plate removed to expose the linkage.
Figure 46:
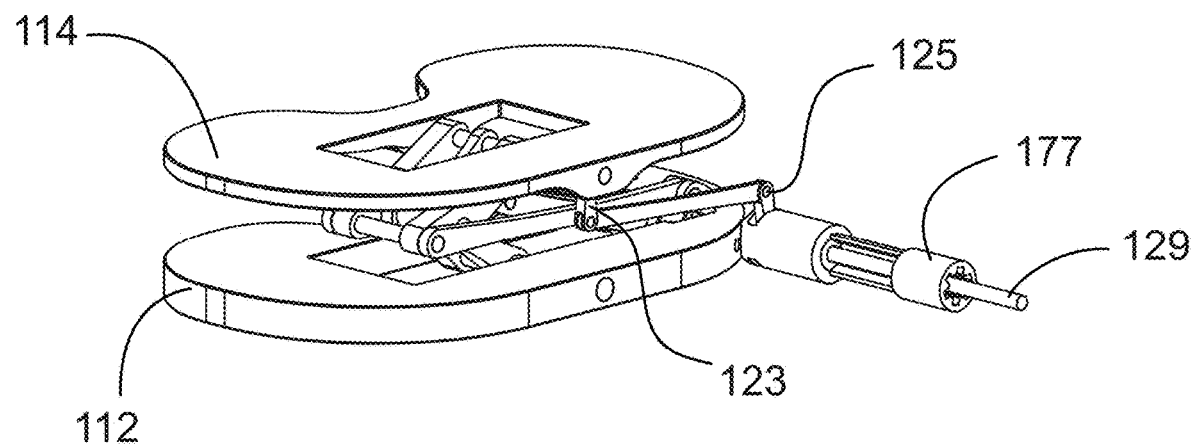
FIG. 46 is a perspective view of the tensioner-balancer of FIG. 44.

FIGS. 45 and 46 show a further modification of the tensioner-balancer 110 to facilitate measuring displacements. A measuring linkage 123 is connected to the top plate 114. As the top plate 112 pivots about axis P, the measuring linkage 123 follows it. The measuring linkage 123 is connected to a crank 125 which is in turn connected to a indicating shaft 129. The indicating shaft 129 is coaxial to the input shaft 177. The measuring linkage 123 is arranged such pivoting movement of the top plate 114 results in rotation of the indicating shaft. The movement of the indicating shaft 129 may be observed visually, or it may be detected by a sensor such as an RVDT or rotary encoder or resolver, which may be part of an instrument described below. This permits measurement of plate angle and/or vertical position.

Figure 17:
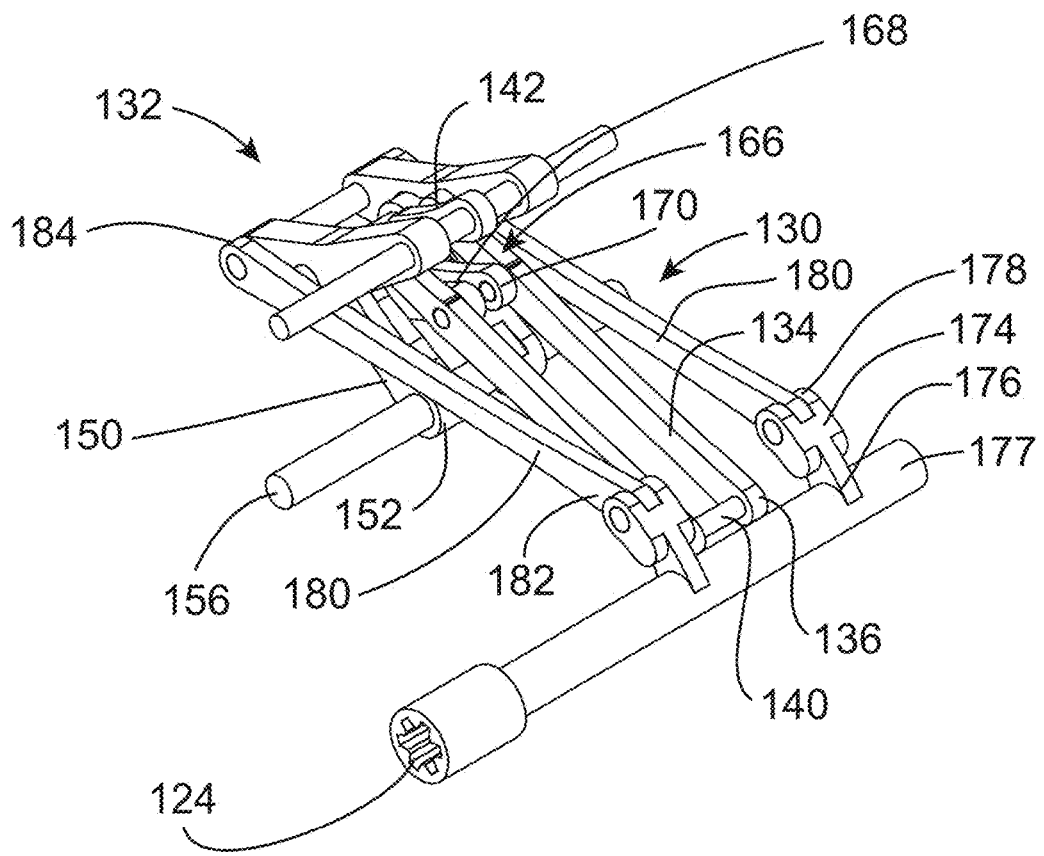
FIG. 17 is another perspective view of the internal linkage shown in FIG. 13.
Figure 18:
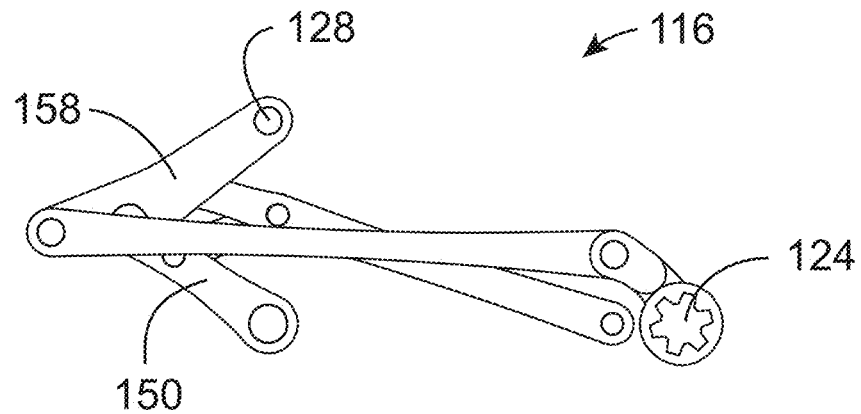
FIG. 18 is a front elevation view of the internal linkage shown in FIG. 13.
Figure 19:
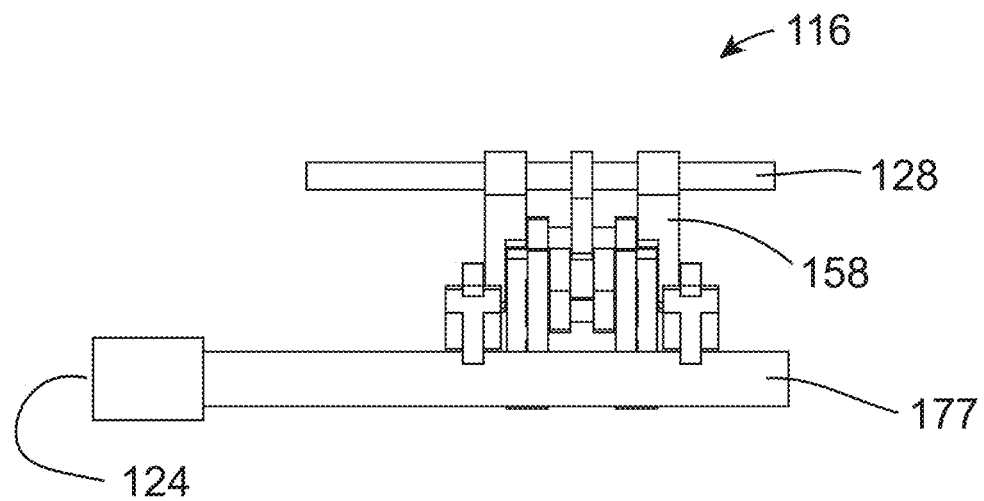
FIG. 19 is an end elevation view of the internal linkage shown in FIG. 13.
Figure 20:
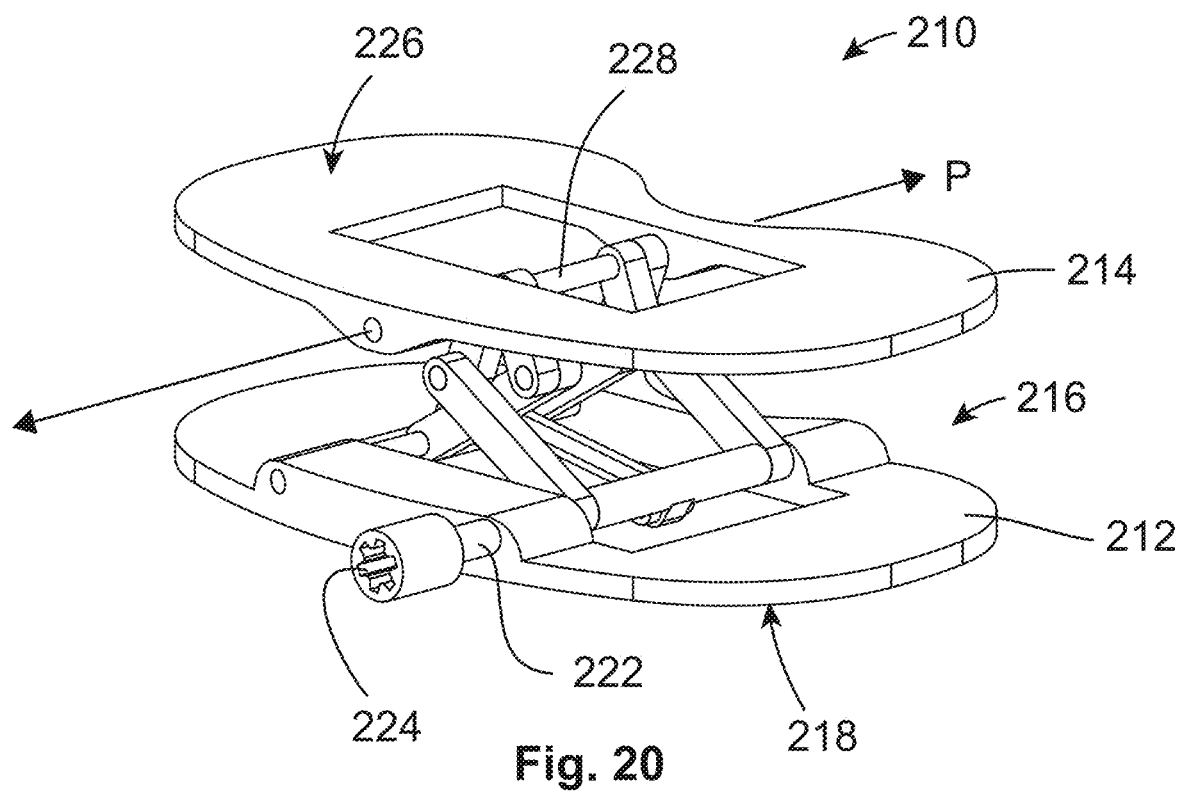
FIG. 20 is a perspective view of an exemplary tensioner-balancer, in an extended position.
Figure 21:
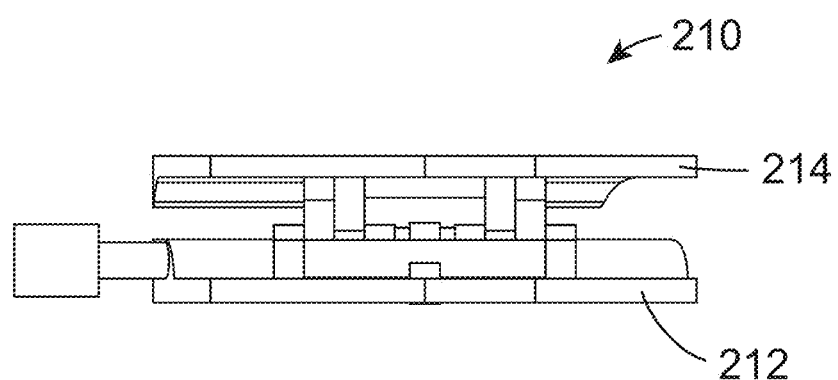
FIG. 21 is a side elevation view of the tensioner-balancer of FIG. 20.
Figure 22:
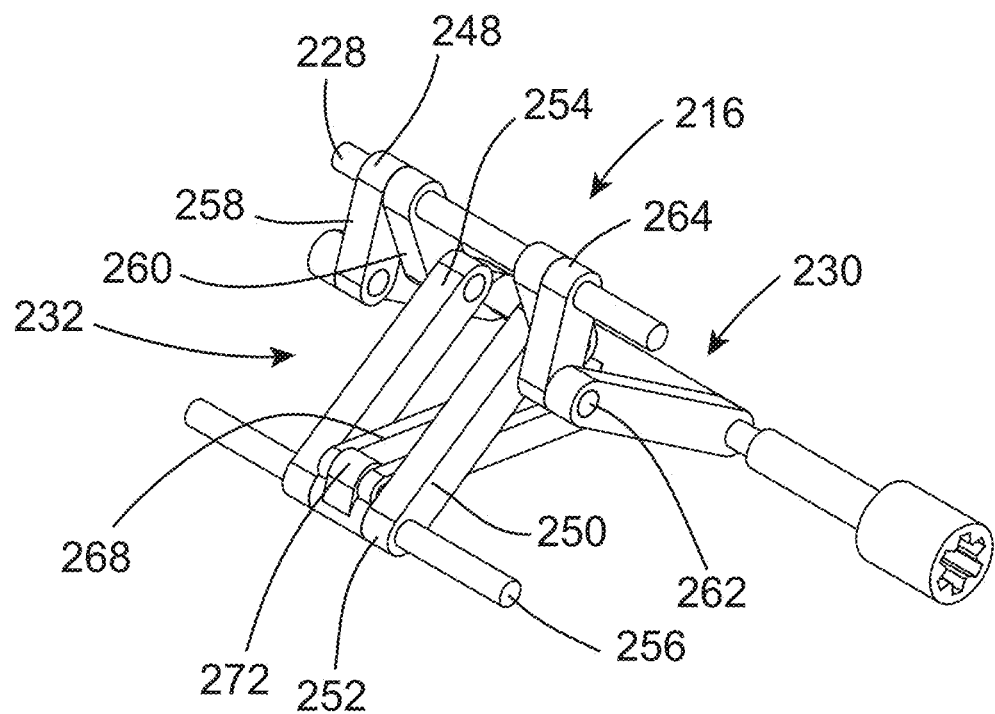
FIG. 22 is a perspective view of the internal linkage of the tensioner-balancer of FIG. 20.
Figure 23:
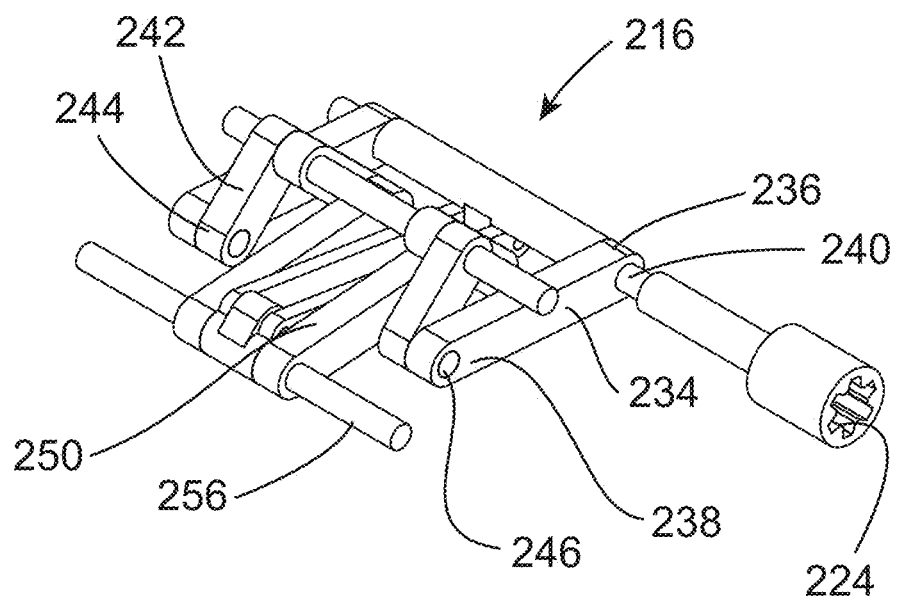
FIG. 23 is another perspective view of the internal linkage shown in FIG. 20.
Figure 24:
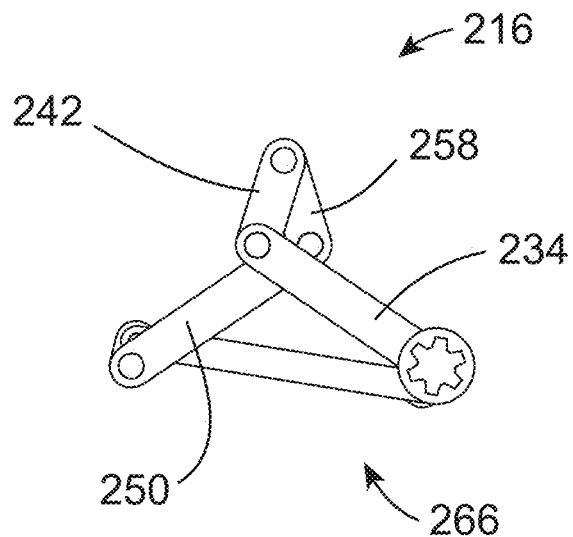
FIG. 24 is a front elevation view of the internal linkage shown in FIG. 20.
Figure 25:
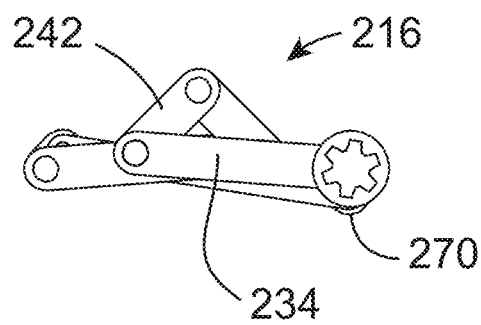
FIG. 25 is another front elevation view of the internal linkage shown in FIG. 20.
Figure 26:
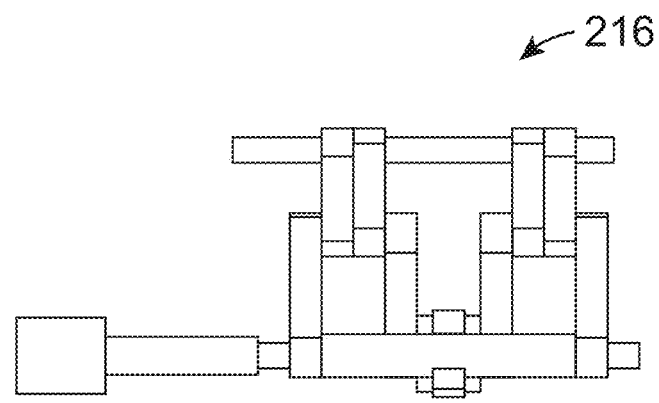
FIG. 26 is an end elevation view of the internal linkage shown in FIG. 23.
Figure 47:
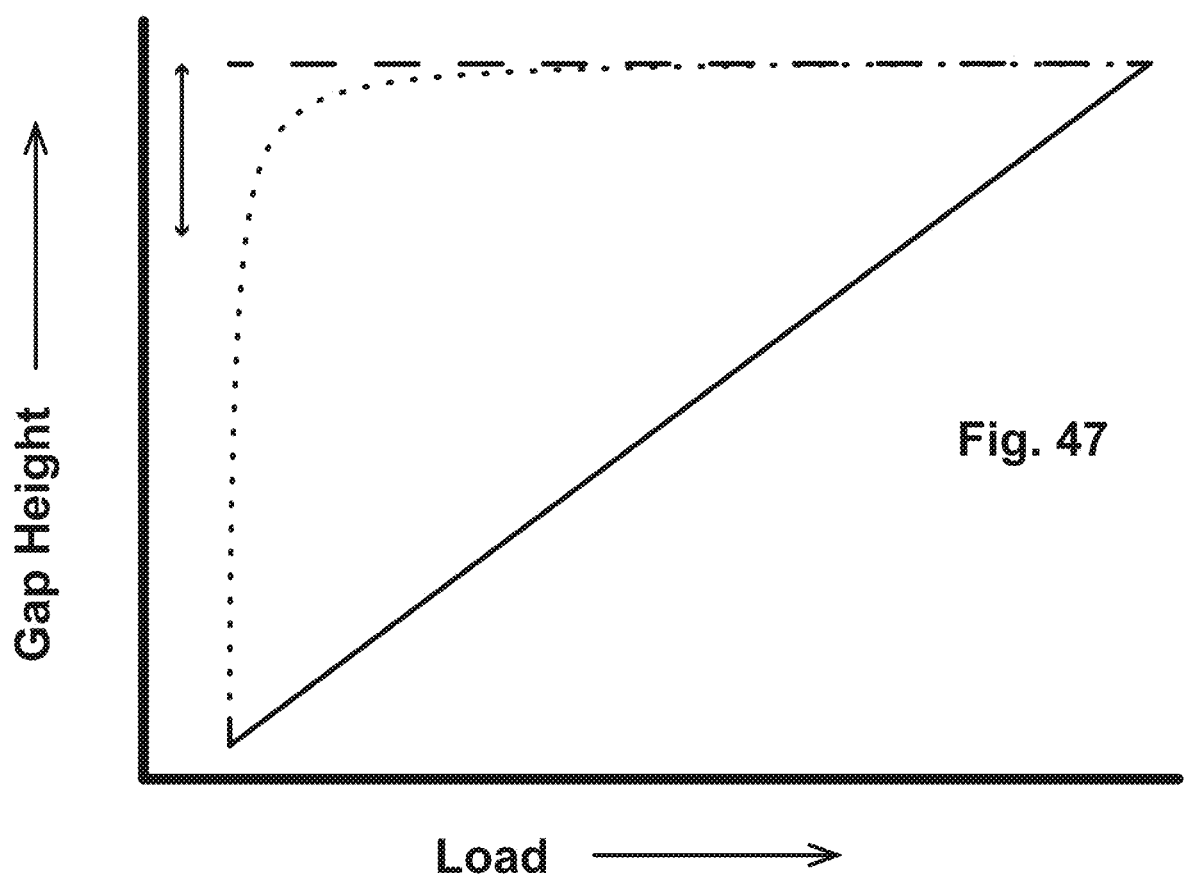
FIG. 47 is a schematic graph of a force-displacement curve of ligaments in a human knee joint.

As noted above, the tensioner-balancer 10 is useful for balancing the gap in a human knee joint when performing a total knee arthroplasty. The use of the tensioner-balancer 10 may be better understood by considering the characteristics of the human knee joint, particularly of the soft tissue (e.g.

ligaments). FIG. 47 is a representative diagram of knee joint gap height versus applied extension load, similar to a stress-strain plot. In FIG. 17, the solid line is representative of properties of a perfectly elastic member (e.g. a rubber band). The dashed line is representative of the properties of a hypothetical infinitely rigid member. The dotted line is representative of the properties of a human knee joint ligament. It can be seen that the ligament is quite stiff and exhibits a low elongation to failure. The vertical portion of the dotted line indicates the range of motion where a minimal applied load will take up all available slack in the ligament. The slope of the gap height/load curve then rapidly transitions through the arcuate corner in the dotted line, to a very rigid characteristic. Given these properties, it will be apparent that the application of a relatively small load will ensure that the ligament is at full extension. In one example, an extension load of about 300 N or less may be applied. It will be understood that the chart in FIG. 46 is general in nature, and that specific ligaments in specific joints may have different magnitudes of slack available, or stated another way, the length of the vertical segment of the dotted line will vary from joint to joint and ligament to ligament. For example, in one patient's knee joint, all slack may be taken up at a relatively small gap height such as 8 mm. In another patient's knee joint, all slack may be taken up at a relatively larger height such as 20 mm.

Numerous instruments may be provided which are suitable for applying actuation loads of this magnitude to the tensioner-balancer 10, as well as indicating, measuring, or recording physical properties of the tensioner-balancer 10 such as position, applied load, and/or tilt position.

Figure 48:
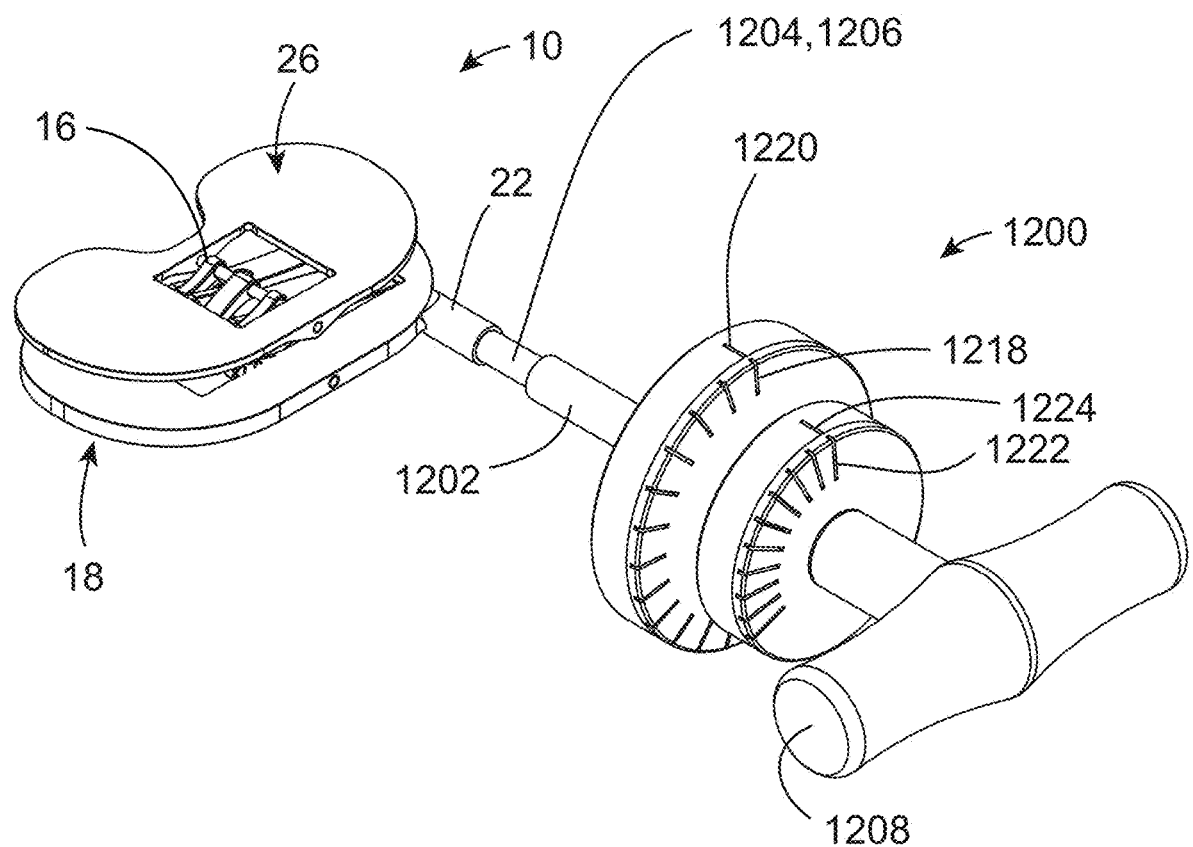
FIG. 48 is a perspective view of the tensioner-balancer of FIG. 1 coupled to a manually-operated actuating instrument.

FIG. 48 illustrates an exemplary actuating instrument 1200 for use with the tensioner-balancer 10. The actuating instrument 1200 includes a barrel 1202. The distal end of the barrel 1202 includes an instrument coupler 1204 defining a second interface 1206 (partially hidden in this view) which is complementary to the first interface 24 of the tensioner-balancer 10. In the illustrated example, the second interface 1206 is configured with external splines.

The actuating instrument 1200 includes a handle 1208 permitting a user to apply torque to the instrument 1200 and thus to the tensioner-balancer 10. Rotation of the handle 1208 will actuate the linkage 16 and cause the tensioner-balancer 10 to move towards the extended position.

The actuating instrument 1200 may include some means for measuring or indicating displacement of the tensioner-balancer 10. In the illustrated example, the barrel 1202 carries a displacement scale 1218 which rotates relative to an index 1220. The displacement scale 1218 may be calibrated to directly indicate the "gap height" of the tensioner-balancer 10 (i.e., the distance between the tibial and femoral surfaces 18, 26).

The actuating instrument 1200 may include some means for measuring or indicating applied force (e.g. joint distraction load) of the tensioner-balancer 10. In the illustrated example, the barrel 1202 carries a load scale 1222 which rotates relative to an index 1224. The load scale 1222 may be calibrated to directly indicate the "distraction load" (i.e. the compressive load between the tibial and femoral surfaces 18, 26) of the tensioner-balancer 10.

Figure 49:
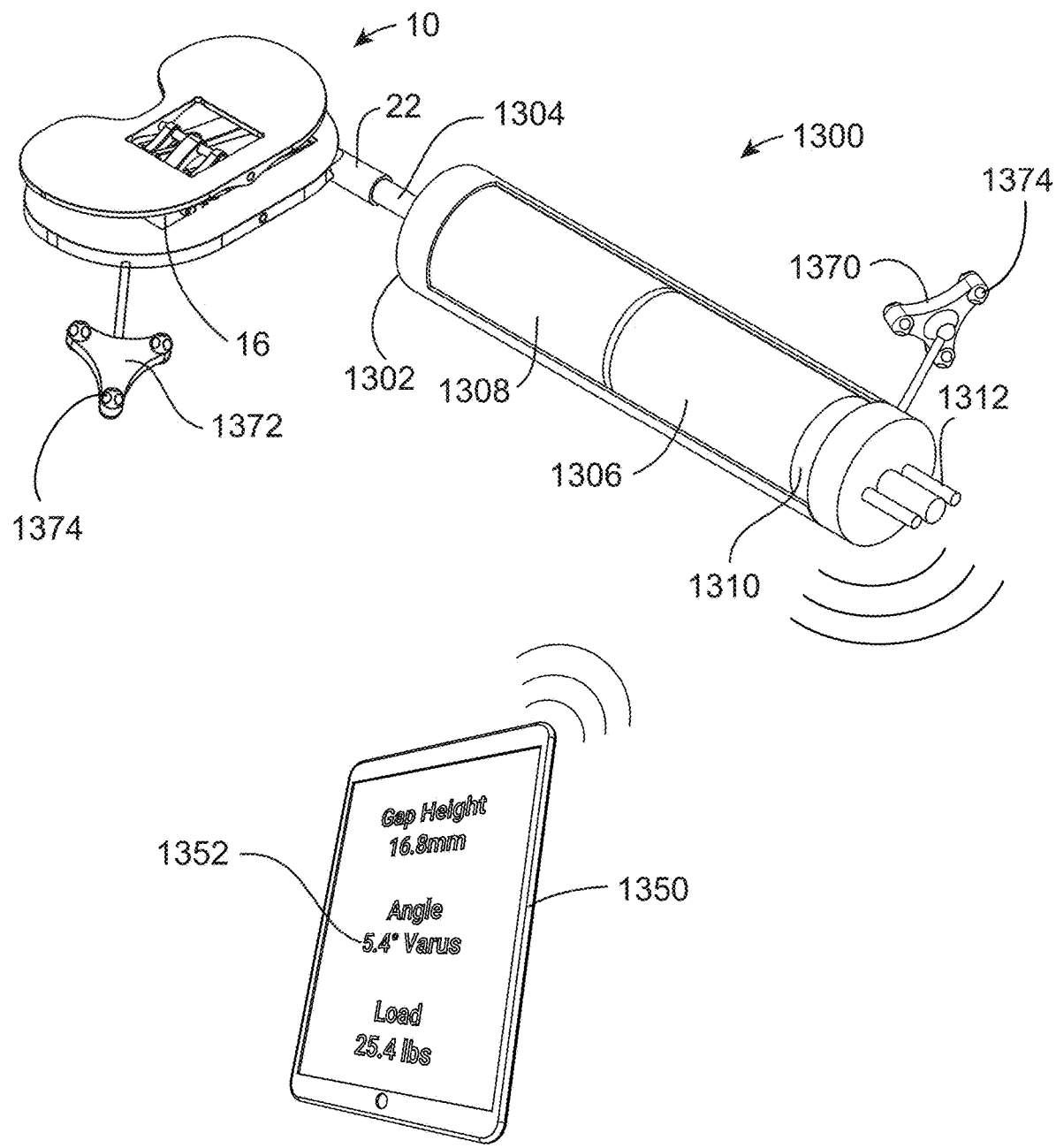
FIG. 49 is a perspective view of the tensioner-balancer of FIG. 1 coupled to a powered actuating instrument.
Figure 50:
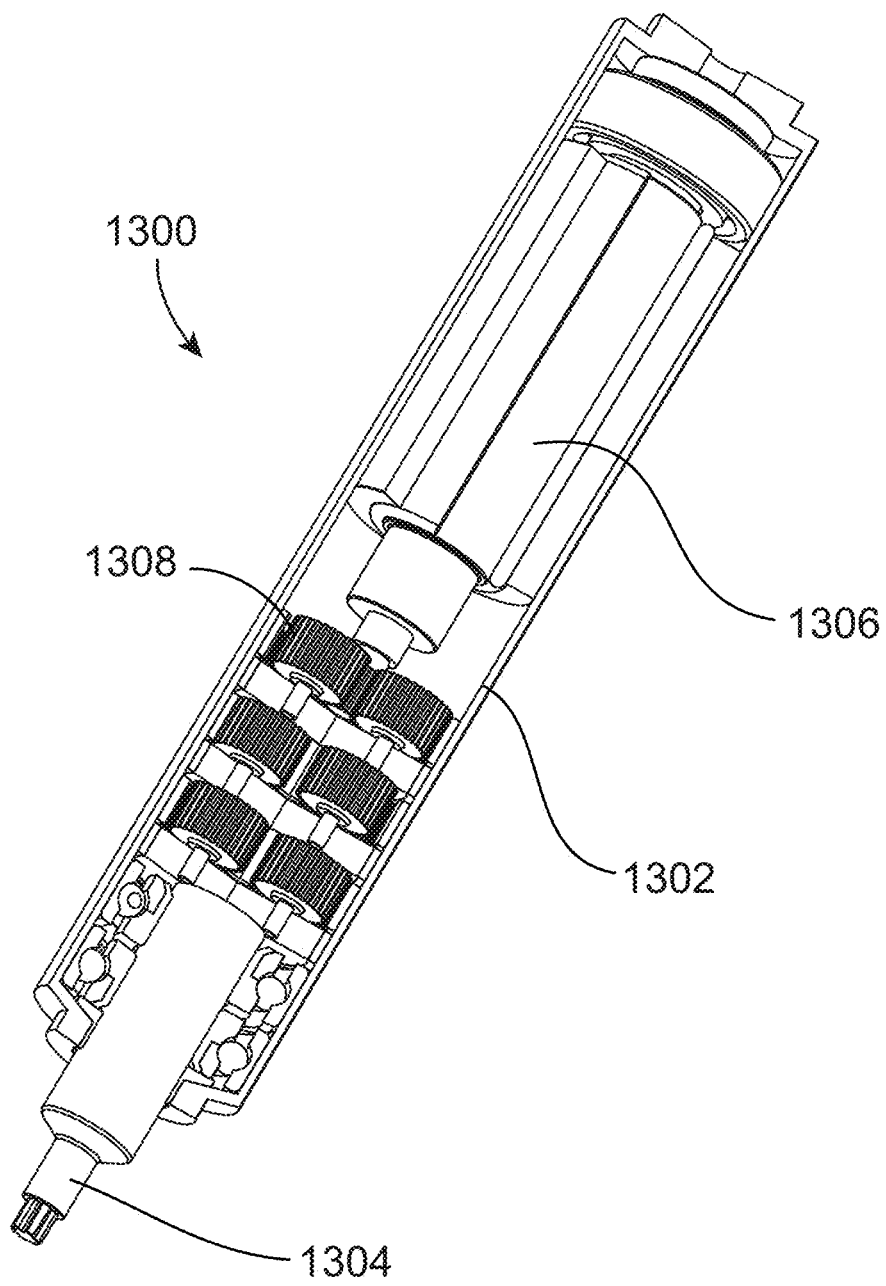
FIG. 50 is a perspective cutaway view of the powered actuating instrument of FIG. 49.

FIGS. 49 and 50 illustrate another exemplary actuating instrument 1300 for use with the tensioner-balancer 10. The actuating instrument 1300 includes a barrel 1302 with an instrument coupler 1304 at its distal end. The interior of barrel 1302 includes (FIG. 50) an appropriate internal mechanism to apply torque to the instrument coupler 1304, such as a stepper motor 1306 including a rotary encoder coupled to a planetary gearset 1308, and control electronics 1310.

The internal mechanism is operable to apply an actuating load to the tensioner-balancer 10. The actuating instrument 1300 includes an electronic data transceiver, shown schematically at 1312. The transceiver 1312 may operate over a wired or wireless connection. The actuating instrument 1300 may be supplied with an appropriate combination of transducers (not shown in FIG. 49) to detect physical properties such as force, tilt angle, and/or applied load and generate a signal representative thereof. For example, the tensioner 10 may be provided with sensors operable to detect the magnitude of extension (i.e. "gap height"), the angle of the top plate about the pivot axis (i.e. varus/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers. (Alternatively, the tensioner-balancer 10 may be provided with simple visual scales, not shown, for displacement/gap height and/or tilt angle, or may include a mechanical linkage, not shown, which can transmit movement representative of tilt angle to a mechanical or electronic actuating instrument). Displacement of the tensioner-balancer 10 may be derived from the encoder signals, knowing the kinematics of the linkage 16. The transceiver 1312 is operable to transmit the signal. A remote display 1350 is configured to receive the signal and produce a display 1352 of the transducer data. As one example, the remote display 1350 may be embodied in a conventional portable electronic device such as a "smart phone" or electronic tablet with suitable software programming. Optionally, the remote display 1350 or other suitable transmitting device may be use to send remote operation commands to the actuating instrument 1300.

In use, the remote display 1350 permits the surgeon to observe the physical properties of the tensioner-balancer 10 in real time as the actuating instrument 1300 is used to operate the tensioner-balancer 10.

Optionally, the actuating instrument 1300 and/or the tensioner-balancer 10 may incorporate tracking markers 1370, 1372 respectively. Each tracking marker includes one or more tracking points 1374 which may be configured as transmitting antennas, radiological markers, or other similar devices. Using an appropriate receiving device such as remote display 1350, the position and orientation of the receiving device to the tracking markers 1370, 1372 may be determined by receipt and analysis at the receiving device of signals transmitted by the tracking markers 1370, 1372. Tracking markers 1370, 1372 and appropriate receivers are known within the state-of-the-art.

Figure 51:
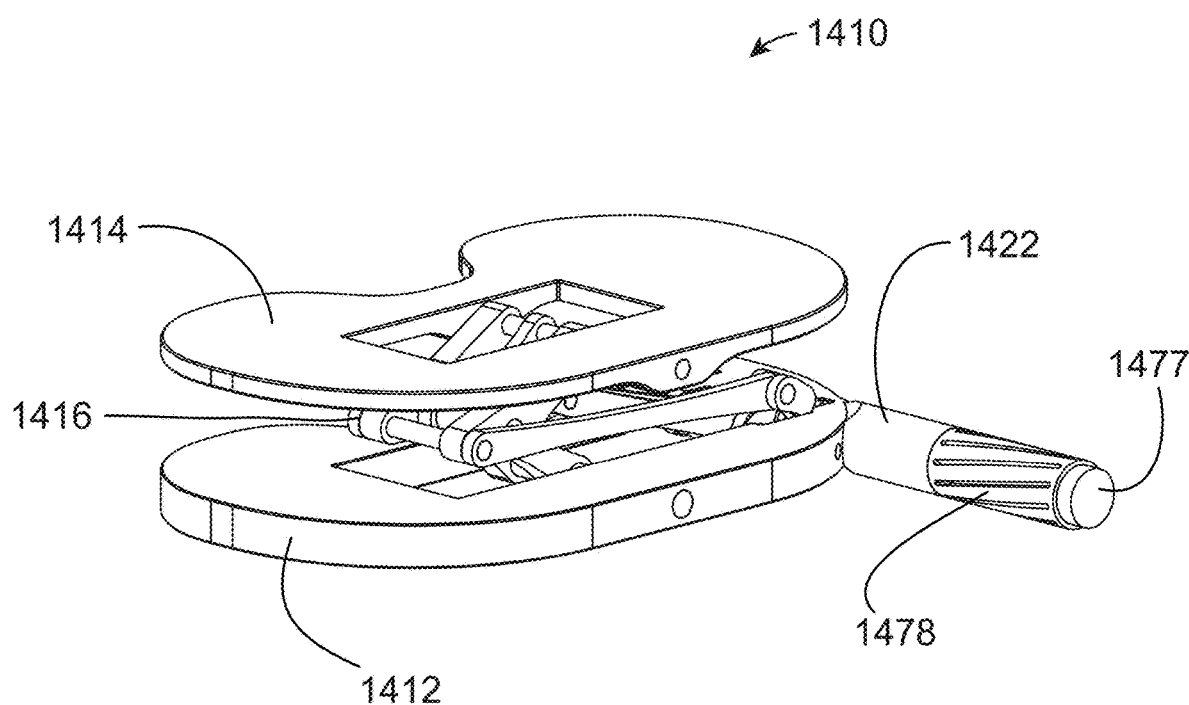
FIG. 51 is a perspective view of an exemplary constant-force tensioner-balancer.

FIG. 51 illustrates an alternative tensioner-balancer 1410 similar in overall construction to the tensioner-balancer 10 described above. It is a standalone device using a "constant force torsion spring". The tensioner-balancer 1410 comprises a baseplate 1412 and a top plate 1414 interconnected by a linkage 1416. The linkage 1416 and the tensioner-balancer 1410 are movable between a retracted position in which the top plate 1414 lies close to or against the baseplate 1412 and an extended position in which the top plate 1414 is spaced away from the baseplate 1414. A coupler 1422 extends from the baseplate 1412, and an input shaft 1477 extends from the coupler 1422. The coupler 1422 and the input shaft 1477 are interconnected by a torsion spring 1478. The linkage 1416 and the input shaft 1477 are configured such that rotation of the input shaft 1477 results in translation of the top plate 1414 relative to the baseplate 1412. Conversely, translation of the top plate 1414 relative to the baseplate 1412 will cause rotation of the input shaft 1477. As the torsion spring 1478 is coupled between the input shaft 1477 and the coupler 1422, compression of the top plate 1414 and the baseplate 1412 will cause torsional deflection (i.e., windup) of the torsion spring 1478, resulting in a reaction force pressing the top plate 1414 and baseplate 1412 apart. The torsion spring 1478 may be configured with a variable spring rate such that the force between the top plate 1414 and baseplate 1412 is constant or nearly constant over a range of movement.

It is optionally possible, in conjunction with tracking markers described elsewhere herein or separately, to use one or more force transducers to collect data representative of the outer shape or profile or geometry of the articular surface of the femoral condyle. The tensioner-balancer 110 illustrated in FIG. 40 includes a pair of spaced-apart load pads 1500 attached to the top plate 114 thereof. Each load pad 1500 includes a transducer operable to detect an applied force and produce a signal proportional to the applied force and/or pressure. Optionally, each of the load pads 1500 may detect and produce a signal representative of (e.g., proportional to) displacement and/or position (e.g., height). Non-limiting examples of transducers effective to produce a signal include strain gauges, or miniature linear variable differential transformers (LVDT), or piezoelectric transducers. The load pads 1500 may be integrated into the top plate. The load pads 1500 are segmented into at least a 2D or two-axis array of sensor elements, e.g., a matrix which is addressable by X, Y reference, radial coordinates, or other suitable position location. The size of the individual sensor elements in the arrays may be selected as required to produce useful and actionable information. The load pads 1500 may be connected to an electronic receiving device as described elsewhere herein by a wired or wireless connection. Appropriate processors and software may be provided for interpretation of the signals from the load pads 1500.

Figure 52:
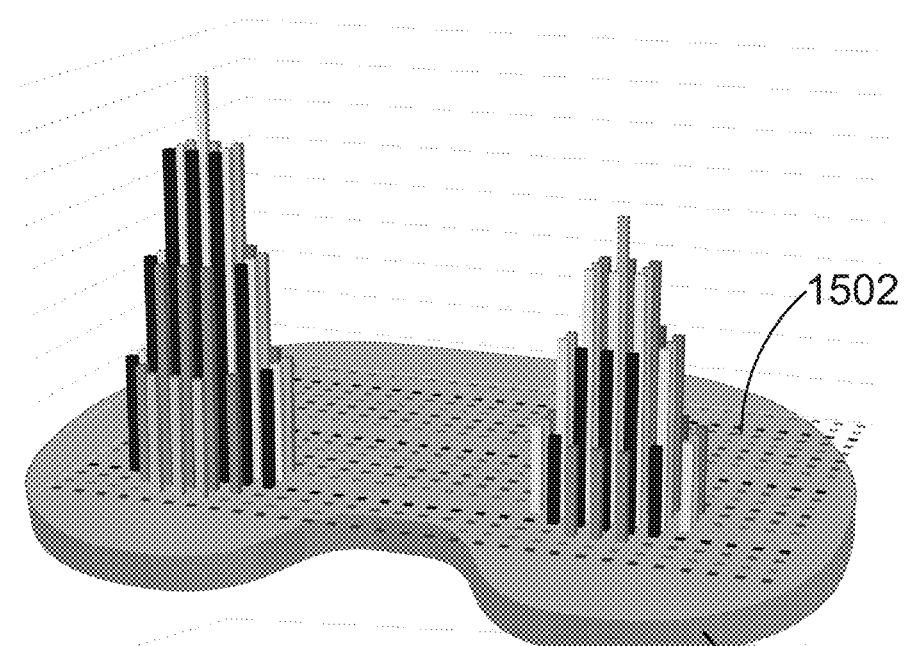
FIG. 52 is a graph showing representative data produced by sensor of a gap balancer, with a knee joint in the fully extended position.

FIG. 52 shows a 3D bar graph of force magnitude (Z-direction height) produced by the femoral condyle (not shown) for each sensor element 1502 superimposed on the image of the femoral interface surface. The illustrated image shows two primary contact zones representing the contact of each femoral condyle on the surface of the device or the contact force between the femoral condyles and the corresponding tibial plateaus (the graphs would look very similar). It can be seen that this data can be used to map the geometry and/or position of the femoral condyle. This mapping may be carried out, for example by inserting the gap balancer 10 between the femur F and the tibia T, and moving the knee joint J through some or all of its range of motion while recording data from the sensor elements 1502 using the electronic receiving device to collect the force data and (optionally) to collect position data from at least one tracking marker. If tracking marker data is also collected, the force data would be correlated to the position data. In other words, the tracking marker data may be used to confirm the joint extension/flexion position at which force data is being collected.

Figure 53:
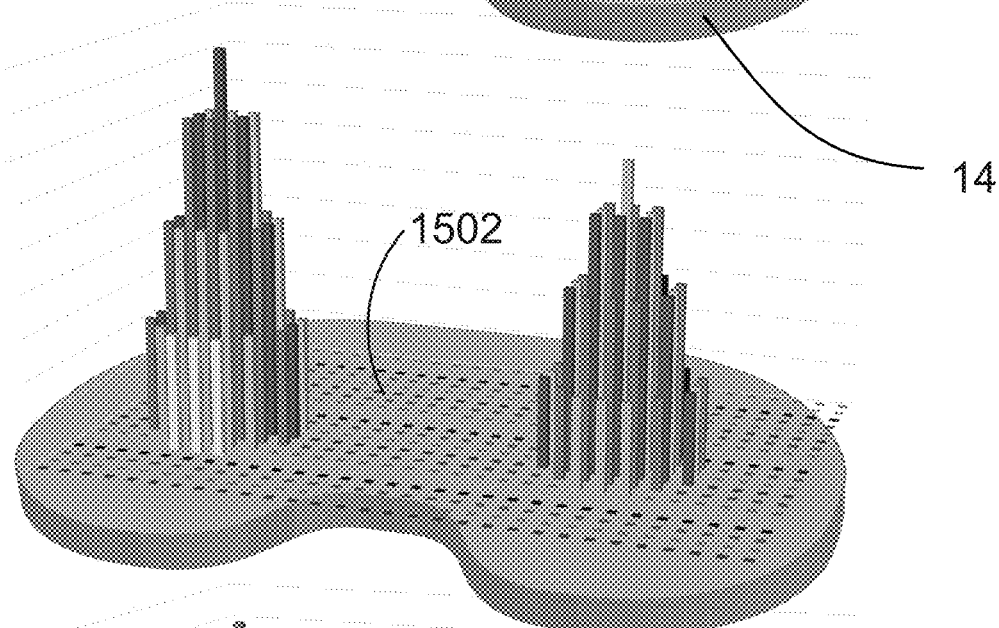
FIG. 53 is a graph showing representative data produced by sensor of a gap balancer, with the knee joint in a mid-flexion position.
Figure 54:
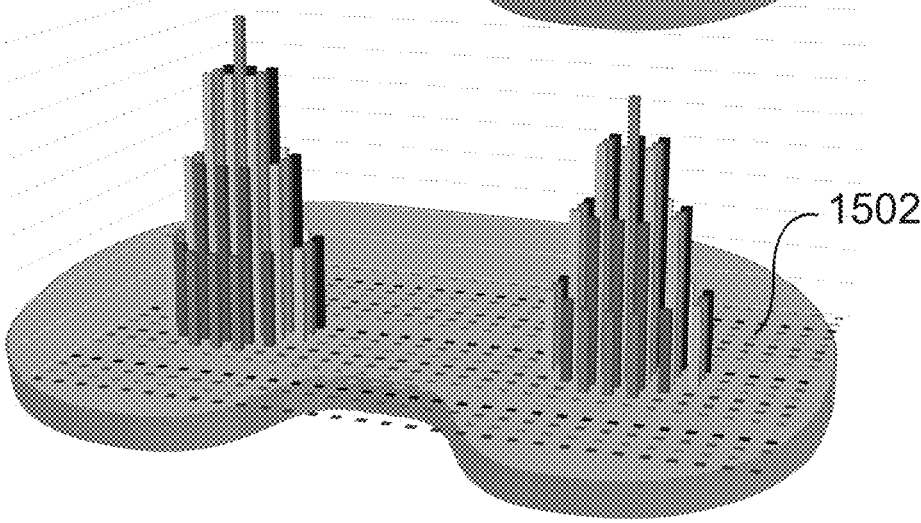
FIG. 54 is a graph showing representative data produced by sensors of a gap balancer with the knee joint in a 90-degree flexed position.

FIG. 53 shows representative force data produced by the two condyles with the knee joint J in a fully extended position. FIG. 52 shows representative force data produced by the two condyles of the knee joint J in a mid-flexion position, for example flexed approximately 45° away from the fully extended position. Finally, FIG. 53 shows representative force plots produced by the two condyles with the knee joint J in a 90-degree flexed position.

Figure 55:
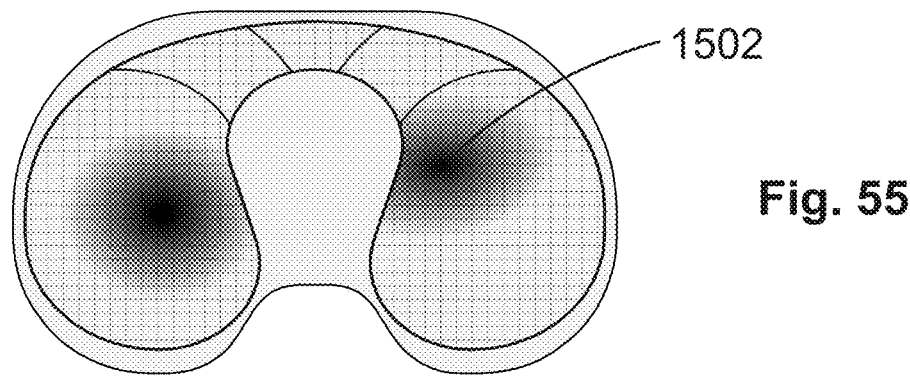
FIG. 55 is a plot showing instantaneous medial and lateral contact patches of the human knee joint, with the knee in the fully extended position.
Figure 56:
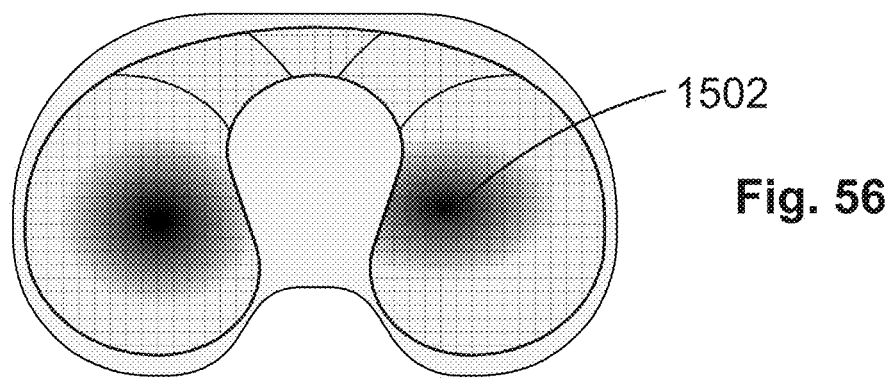
FIG. 56 is a plot showing instantaneous medial and lateral contact patches of the human knee joint, with the knee in a mid-flexion position.
Figure 57:
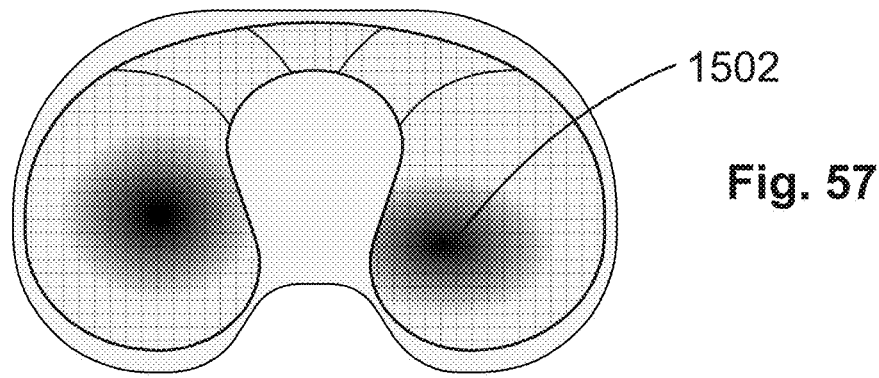
FIG. 57 is a plot showing instantaneous medial and lateral contact patches of the human knee joint, with the knee in a 90-degree flexed position.

FIGS. 55-57 show examples of force data represented as a 2D surface plot. This is another means of illustrating the instantaneous medial and lateral contact patches between the femoral condyles in the tibial plateaus. In this view, the medial contact patch is to the left and the lateral contact patch is to the right. In these views, darker areas indicate relatively higher force or pressure, and lighter colors indicate relatively lower force or pressure. The movement of the contact patches may be readily visualized as the knee joint J is moved from a fully extended position (FIG. 55) through a 45-degree mid-flexion position (FIG. 56) to a 90-degree flexion position (FIG. 57).

Figure 58:
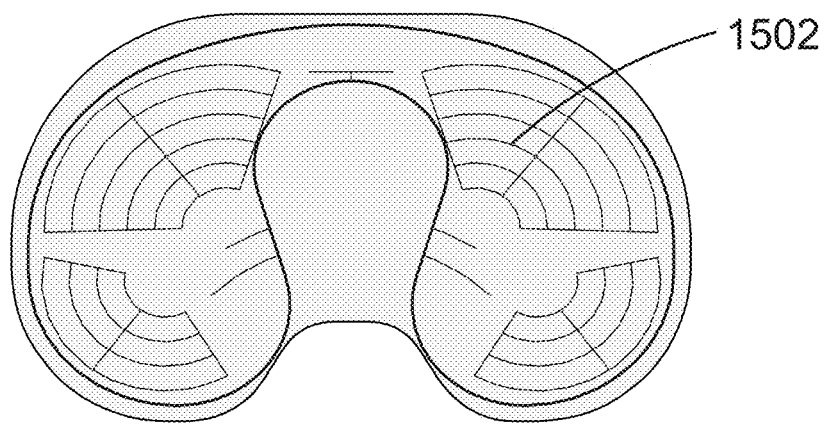
FIG. 58 is a schematic showing an example of sensors arrayed as arcuate segments.
Figure 59:
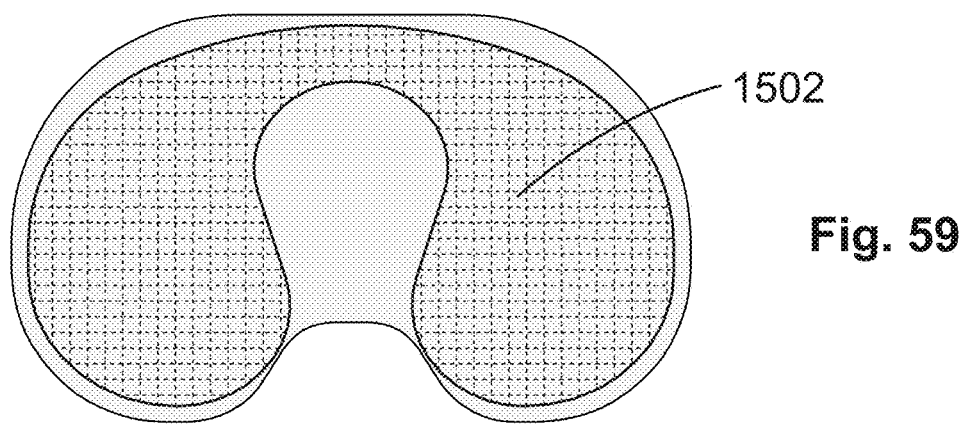
FIG. 59 is a schematic showing sensors arrayed in a 2D grid pattern.
Figure 60:
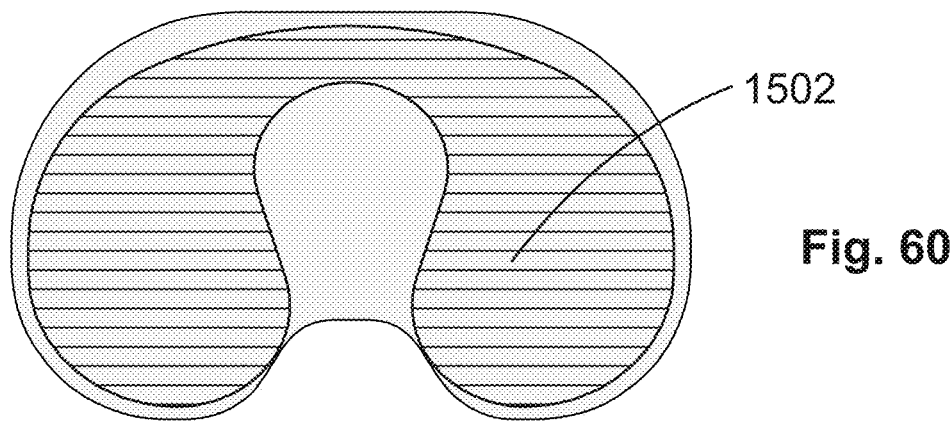
FIG. 60 is a schematic showing sensors arrayed as a series of parallel strips or bands.

In FIGS. 55-57, the sensor array is shown configured in an orthogonal X-Y grid pattern. The sensor pattern may be configured to suit a particular application. FIG. 58 shows an example of sensors arrayed as arcuate segments. FIG. 59 shows sensors arrayed in a 2D grid pattern, and FIG. 60 shows sensors arrayed as a series of parallel strips or bands.

Figure 61:
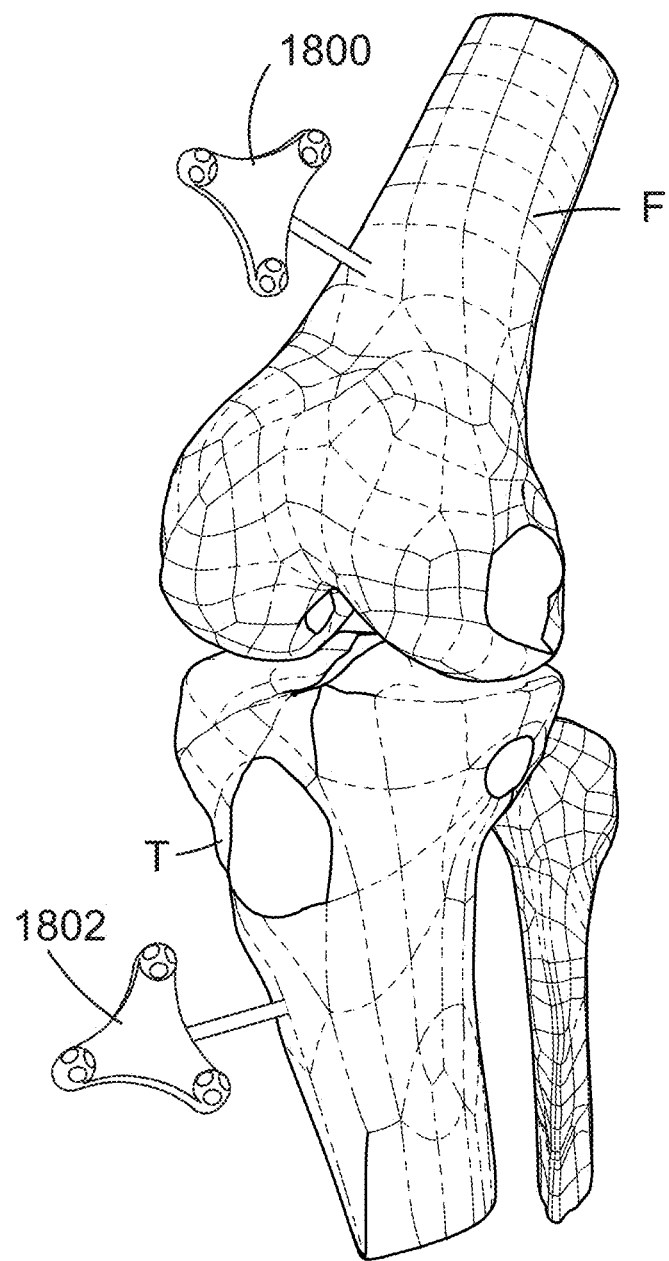
FIG. 61 is a perspective view of a knee joint with tracking markers attached thereto.

The tracking markers described above can be used in conjunction with other tracking markers to perform surgical processes using local, relative navigation. An example configuration is shown in FIGS. 61-63. In this example configuration, a tracking marker 1800 (similar to tracking marker 1370 described above) is attached to the femur F in such a way that as a substantially fixed position orientation relative to the femur F. Another tracking marker 1802 is attached to the tibia T in such a way that as a substantially fixed position orientation relative to the tibia T.

The tensioner-balancer 110 is inserted into the knee joint J and coupled to the actuation instrument 1300 having a tracking marker 1370 as described above. Alternatively, the tensioner-balancer 110 may be provided with built-in tracking marker 1372.

A receiving device such as remote display 1350 (FIG. 49) is configured to receive the signals and or otherwise track the positions of the tracking markers 1370, 1372, 1800, 1802, and to store, manipulate, and/or display the position data.

Once the tensioner-balancer 110, actuating instrument 1300, and tracking markers 1370, 1372, 1800, 1802 are in place, the leg may be moved to different positions (e.g., extension, flexion, lateral left/right movement), while monitoring the position of tracking markers, thus generating a position track for each of the tracking markers. The recorded position track data may be used for multiple purposes including but not limited to creating computer models of the knee joint J, determining the position and orientation of the knee joint J, determining axes of rotation, computing cutting planes and/or drill axes for surgical procedures, providing guidance for handheld surgical tools, or providing guidance for robotic surgical tools. It is also possible to use the tensioner-balancer to check the status of knee after cuts have been made (against flat cut bony surfaces) and/or after trial or final implants have been installed. Implants could be the actual articular components or artificial tensile members.

Figure 64:
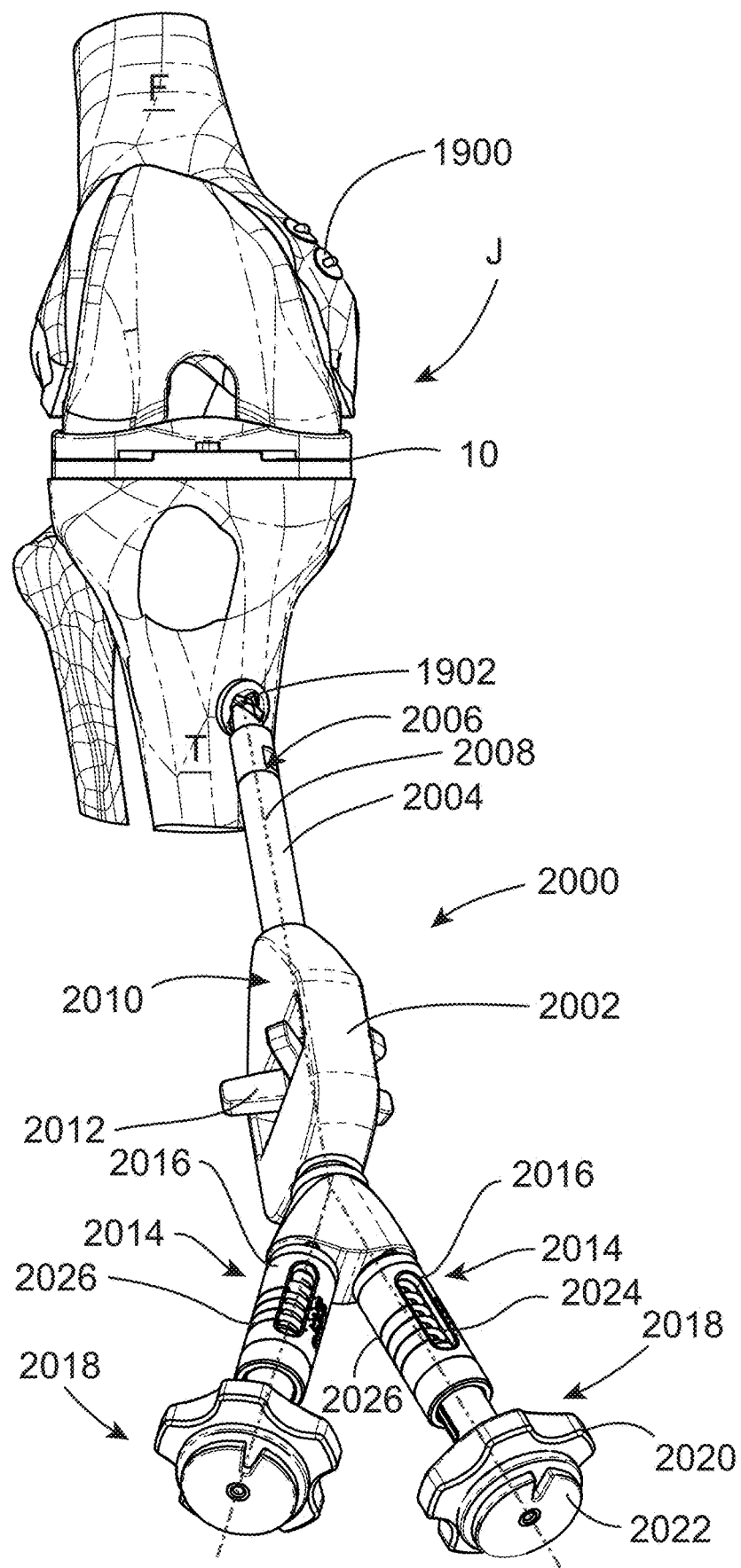
FIG. 64 is a perspective view of a human knee joint showing an artificial tensile member being implanted.

Surgical procedures on the knee joint utilizing the tensioner-balancer 10 may be implemented in conjunction with the implantation of one or more artificial tensile members. FIG. 64 illustrates an exemplary tensile member 1900 along with an insertion instrument 2000 which may be used to insert, tension, and activate swage-type anchors 1902 used to secure the tensile member 1900. The basic components of the insertion instrument 2000 are a body 2002, a stem 2004 extending from the body 2002 and having an anchor connection mechanism 2006 disposed at a distal end thereof, a hollow pushrod 2008 extending through the stem 2004 and slidably movable between retracted and extended positions, and a driving mechanism 2010 for moving the pushrod 508 between retracted and extended positions. The stem 2004 and the pushrod 2008 may be rigid or flexible.

In the illustrated example, the driving mechanism 2010 comprises an internal threaded mechanism which is manually operated by a star wheel 2012.

A tensioner 2014 is part of or connected to the insertion instrument 2000. It has a housing 2016. A shuttle assembly 2018 including an adjustment knob 2020 and a grooved spool 2022 is received inside the housing 2016. A compression spring 2024 is captured between the shuttle assembly 2018 and the housing 2016. The shuttle assembly 518 can translate forward and aft relative to the housing 2016 in response to rotation of the adjustment knob 2020.

In use, a first end of a tensile member 1900 passes through the hollow interior of tensioner 2014 and is secured to the spool 2022. The tension applied to the tensile member 1900 may be indicated, for example, by observing the position of the shuttle assembly 2018 relative to a calibrated scale 2026 on the housing 2016. When a suitable final tension is achieved, the star wheel 2012 may be operated to actuate the pushrod 2008, swaging the tensile member 1900 and fracturing the breakaway structure of the anchor. In the illustrated example, two separate tensioners 2014 are provided, allowing the tension of each of the tensile members to be set independently.

In one example procedure where two tensile members are used, a first provisional tension is applied to the first tensile member and a second provisional tension is applied to the second tensile member. The second tensile member may have the same or different tension at the first tensile member. Next, the provisional tensions evaluated to determined if they are suitable. In response to the evaluation they may be increased or decreased. Finally, the anchor may be swaged to secure the tensile members and finalize the tension. In one example, the tension may be from about 0 N (0 lb.) to about 222 N (50 lb.)

The apparatus and method described herein have numerous advantages over prior art apparatus and techniques.

The tensioner-balancer enables patella-in-place gap balancing during total knee arthroplasty. By allowing the patella (and other soft tissue around the knee space) to remain in its anatomical position during the balancing procedure, a more accurate and anatomically relevant gap can be established.

Furthermore, due to its non-intrusive nature, the tensioner-balancer can enable in-situ gap balancing by means of soft tissue releases (to open one side of the gap relative to the other to make it more "rectangular" and less "trapezoidal") and tension ligament augmentation (to close one side of the gap by tightening or augmenting ligaments to make it more "rectangular" and less "trapezoidal").

The tensioner-balancer 10 is mechanically robust and simple with relatively few parts, enabling it to be effectively sterilized or re-sterilized.

The foregoing has described apparatus and methods for knee gap tensioning. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends, or to any novel one, or any novel combination, of the steps of any method or process so disclosed.

What is claimed is:

1. A knee gap tensioning apparatus, comprising:
   a tensioner-balancer, including:
     a baseplate;
     a top plate; and
     a linkage interconnecting the baseplate and the top plate and operable to move the top plate relative to the bottom plate between retracted and extended positions in response to application of an actuating force, the linkage including:
       a first toggle linkage, including:
         a lower link having a first end and a second end, the first end pivotally connected to the baseplate;
         an upper link having a first end and a second end, the first end pivotally connected to the top plate, wherein the second ends of the first and second links are pivotally connected to each other;
       a second toggle linkage, including:
         a lower link having a first end and a second end, the first end pivotally connected to the baseplate;
         an upper link having a first end and a second end, the first end pivotally connected to the top plate, wherein the second ends of the first and second links are pivotally connected to each other;
       a connector linkage interconnecting the first and second toggle linkages;
     wherein the links of the linkage comprise parallel pivot axes;
     wherein the linkage is configured so as to produce linear movement of the top plate relative to the base plate, in response to a rotational movement of one or more of the links;
   wherein the linkage includes an input shaft coupled to the linkage and configured to accept a rotary input about an axis parallel to the parallel pivot axes of the links of the linkage; and
   at least one sensor operable to measure a distraction load applied by the tensioner-balancer.

2. The apparatus of claim 1, wherein the top plate is pivotally connected to the linkage so as to be able to freely pivot about a single mechanical pivot axis to change its angular orientation relative to the base plate.

3. The apparatus of claim 1, wherein a distraction height of the tensioner-balancer defined as distance between a tibia interface surface of the baseplate and a femoral interface surface of the top plate, in the extended position, is in a range of 8 mm to 20 mm.

4. The apparatus of claim 1, wherein the at least one sensor is configured to measure an input torque to the tensioner-balancer.

5. The apparatus of claim 1, wherein the at least one sensor comprises a stress or strain transducer disposed on the top plate.

6. The apparatus of claim 1, wherein the at least one sensor comprises a stress or strain transducer disposed on at least one of the links.

7. The apparatus of claim 1, wherein the at least one sensor is configured to measure a distraction load on left and right portions of the top plate separately.

8. The apparatus of claim 7, wherein the at least one sensor comprises an array of electronic force sensors.

9. The apparatus of claim 1, further comprising at least one sensor configured to measure a tilt angle of the top plate.

10. The apparatus of claim 9, wherein the at least one sensor configured to measure a tilt angle of the top plate comprises a rotary position sensor that pivots with the top plate.

11. The apparatus of claim 9, wherein the at least one sensor configured to measure a tilt angle of the top plate comprises a linkage that moves dependent on the angle of the top plate, independent of a separation distance between the baseplate and the top plate.

12. The apparatus of claim 1, further comprising: an actuating instrument including an interface complementary to an interface of the tensioner-balancer and a powered mechanism operable to apply the actuating force to the tensioner-balancer.

13. The apparatus of claim 12, wherein the powered mechanism comprises a motor and a gearbox.

14. The apparatus of claim 13, wherein the gearbox comprises a multi-stage planetary gearset.

* * * * *